US011617522B2

(12) United States Patent
Li et al.

(10) Patent No.: US 11,617,522 B2
(45) Date of Patent: Apr. 4, 2023

(54) SENSOR INSERTER WITH DISPOSAL LOCKOUT STATE

(71) Applicant: MEDTRONIC MINIMED, INC., Northridge, CA (US)

(72) Inventors: Xin X. Li, Shanghai (CN); Zhiyong Liu, Shanghai (CN); Matthew William Yavorsky, Granada Hills, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 765 days.

(21) Appl. No.: 16/533,534

(22) Filed: Aug. 6, 2019

(65) Prior Publication Data

US 2021/0038131 A1    Feb. 11, 2021

(51) Int. Cl.
| | |
|---|---|
| *A61B 5/145* | (2006.01) |
| *A61M 5/145* | (2006.01) |
| *A61M 5/172* | (2006.01) |
| *A61B 5/153* | (2006.01) |

(52) U.S. Cl.
CPC ...... *A61B 5/14532* (2013.01); *A61B 5/14546* (2013.01); *A61B 5/153* (2013.01); *A61M 5/172* (2013.01); *A61M 5/14566* (2013.01)

(58) Field of Classification Search
CPC . A61B 5/14532; A61B 5/14546; A61B 5/153; A61M 5/172; A61M 5/14566
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |

(Continued)

*Primary Examiner* — Navin Natnithithadha
*Assistant Examiner* — Meghan R Kumar
(74) *Attorney, Agent, or Firm* — Fortem IP LLP; Mary Fox

(57) ABSTRACT

A sensor inserter for a physiological characteristic sensor includes a housing that defines a track system that extends from a bottom of the housing toward a top of the housing. The sensor inserter includes a striker assembly movable relative to the housing between a first state, a second, cocked state and a third, disposal state. The striker assembly is movable from the second, cocked state to the third, disposal state to couple the physiological characteristic sensor to an anatomy. The striker assembly includes a lock beam that engages with the track system as the striker assembly moves between the first state, the second, cocked state and the third, disposal state. In the third, disposal state the lock beam inhibits movement of the striker assembly from the third, disposal state to the first state.

20 Claims, 31 Drawing Sheets

(56) References Cited

U.S. PATENT DOCUMENTS

| | | |
|---|---|---|
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,892,085 B2 | 5/2005 | McIvor et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,468,033 B2 | 12/2008 | Van Antwerp et al. |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Mair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,101,305 B2 | 8/2015 | Larson et al. |
| 9,295,786 B2 | 3/2016 | Gottlieb et al. |
| 2007/0123819 A1 | 5/2007 | Mernoe et al. |
| 2009/0299301 A1 | 12/2009 | Gottlieb et al. |
| 2010/0160861 A1 | 6/2010 | Causey, III et al. |
| 2017/0188912 A1* | 7/2017 | Halac .................. A61B 5/6832 |
| 2020/0196919 A1* | 6/2020 | Rao .................... A61B 5/14865 |

* cited by examiner

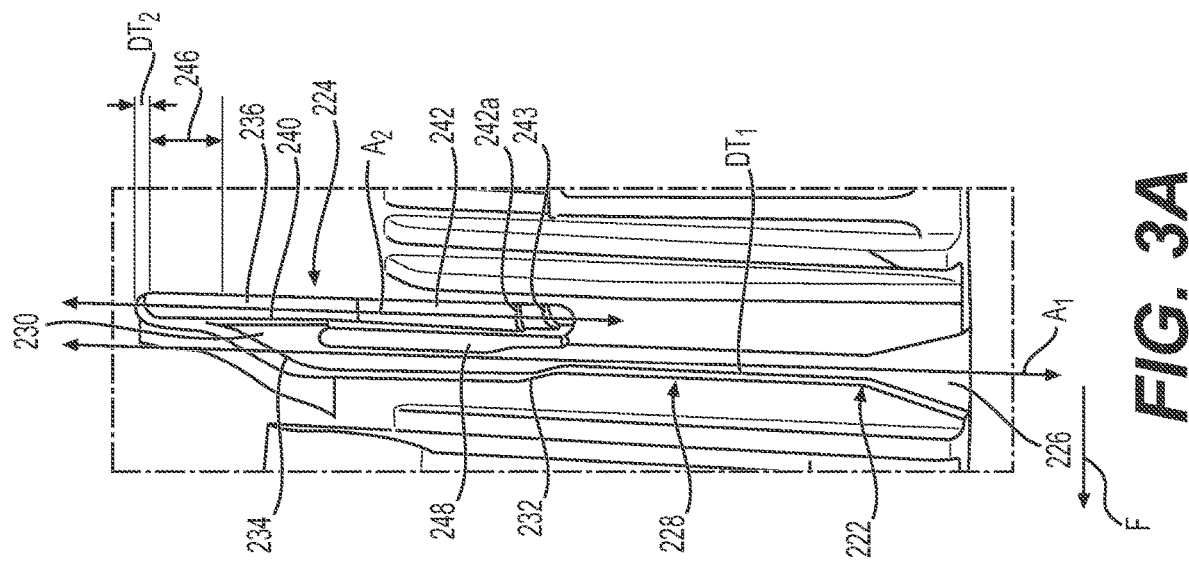
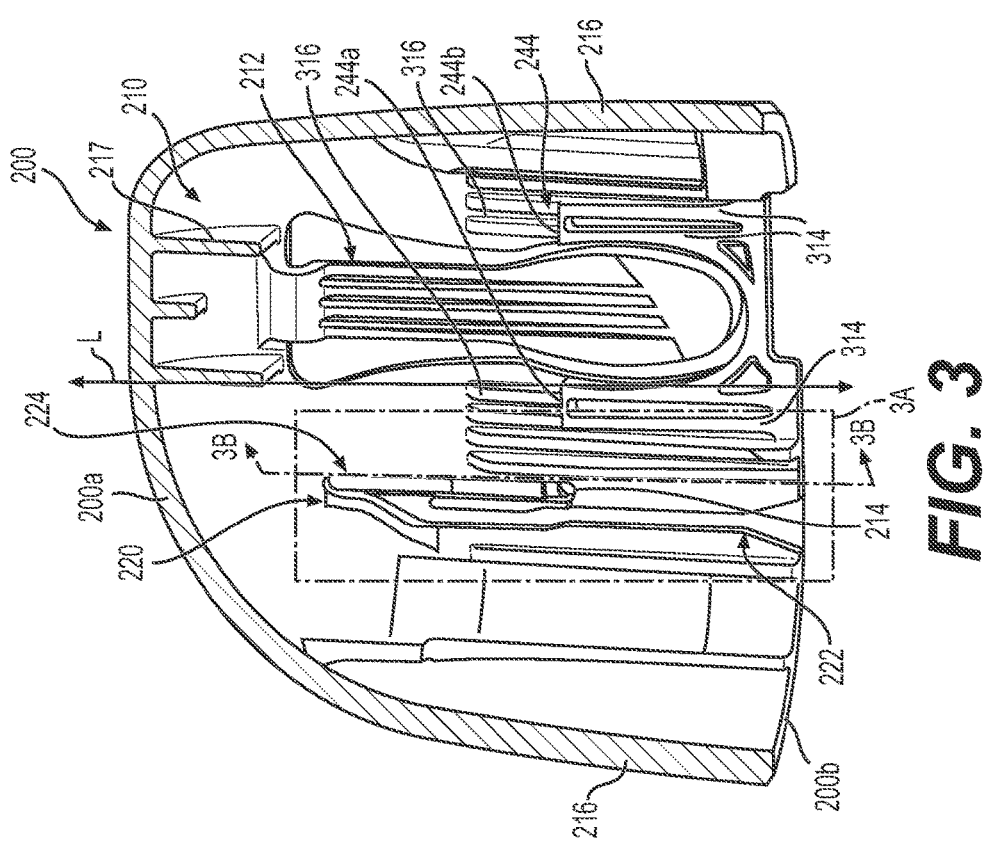

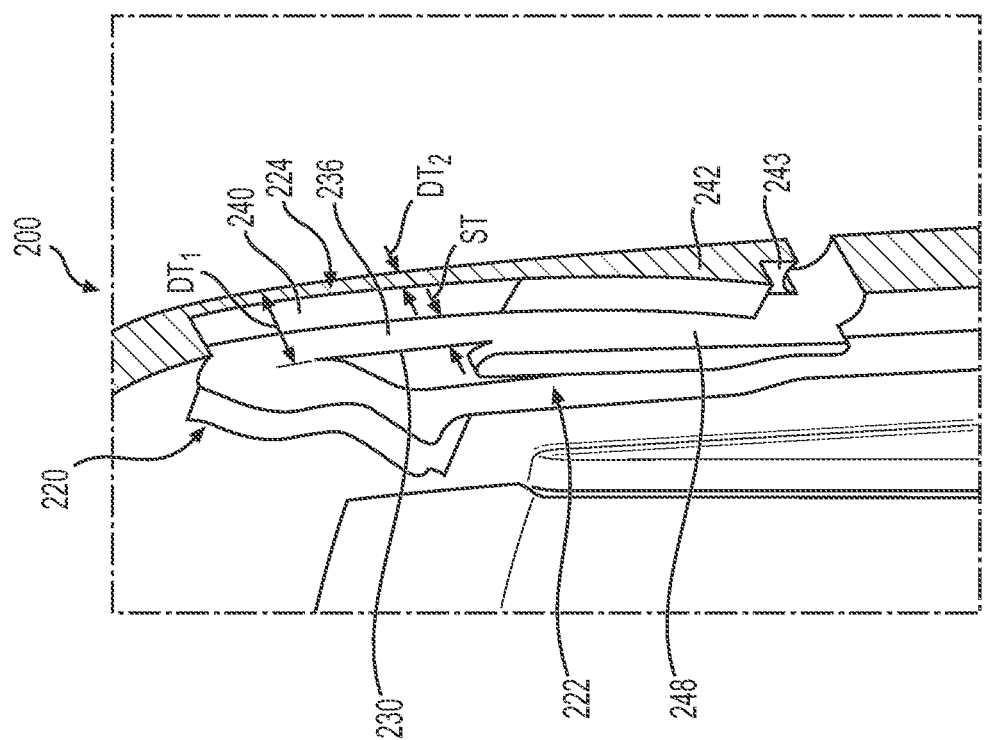

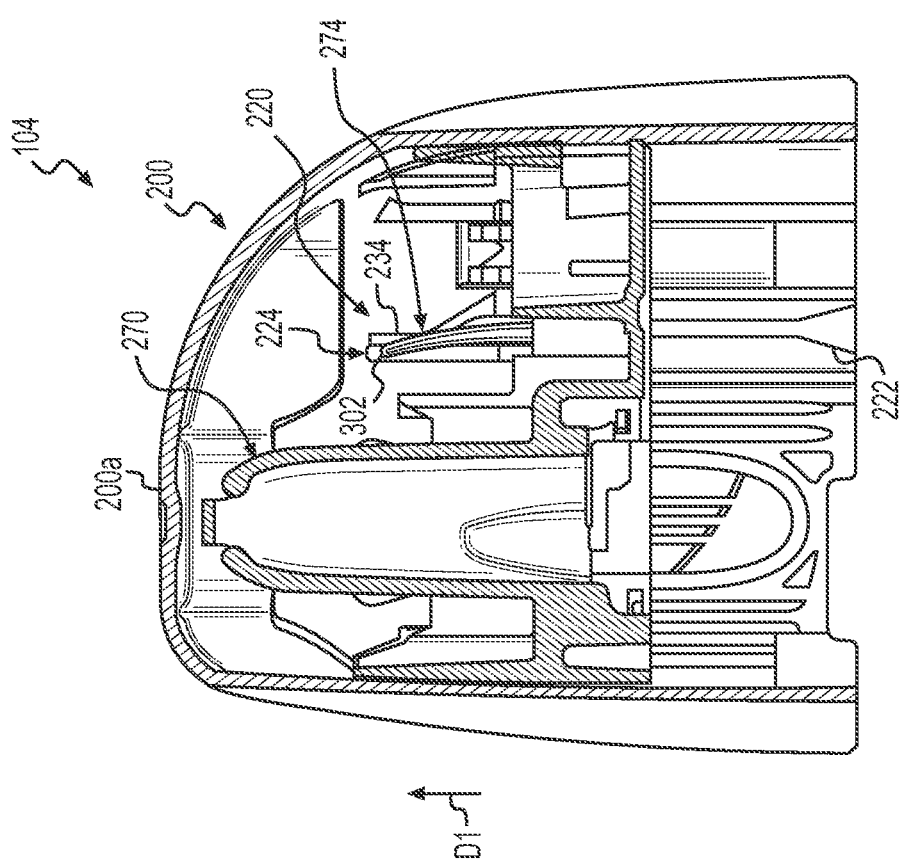

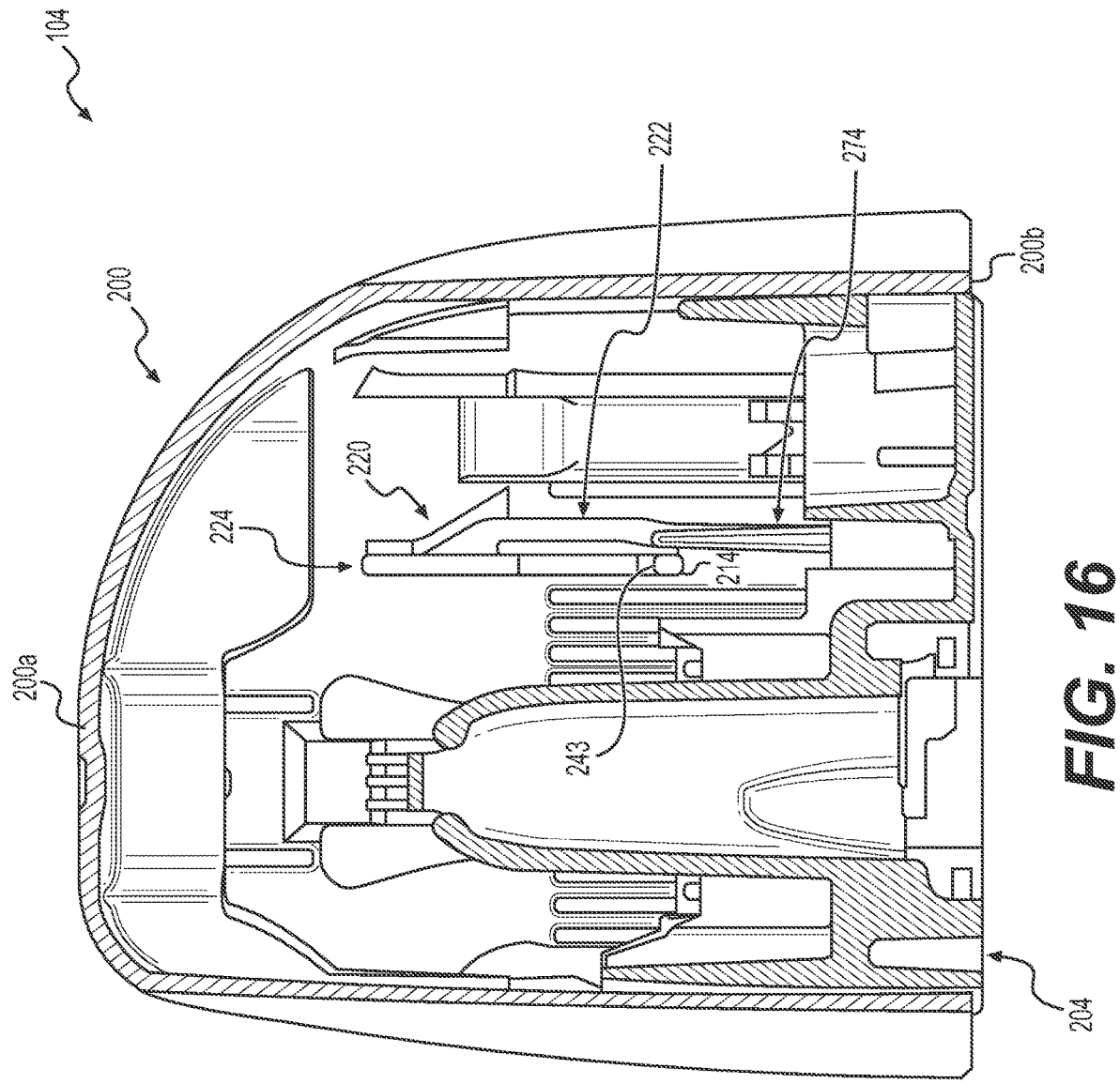

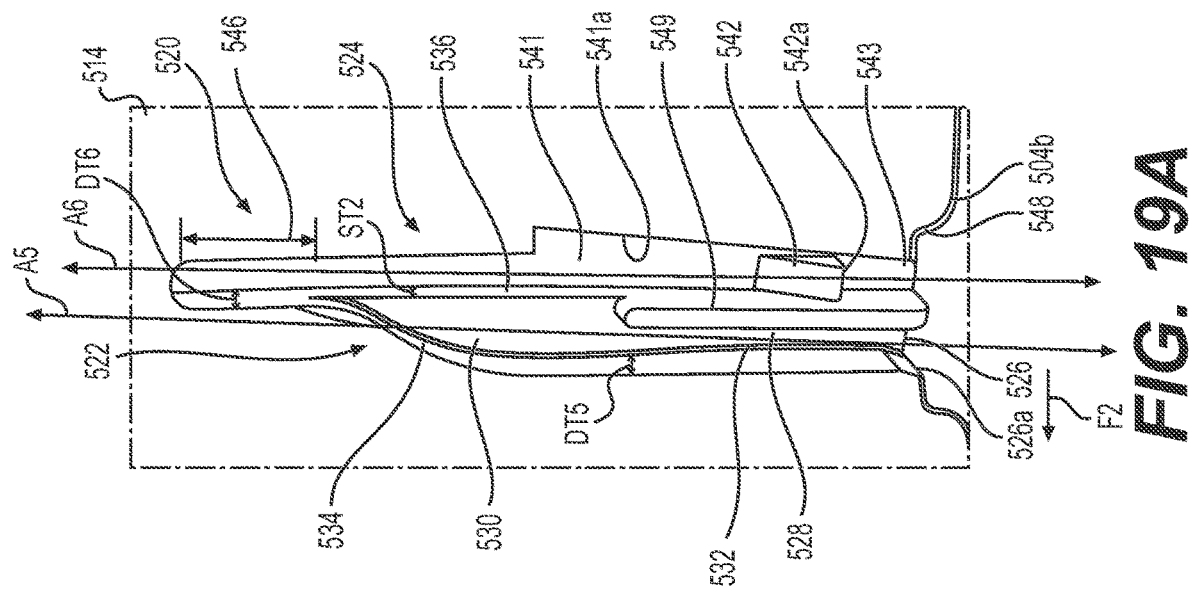
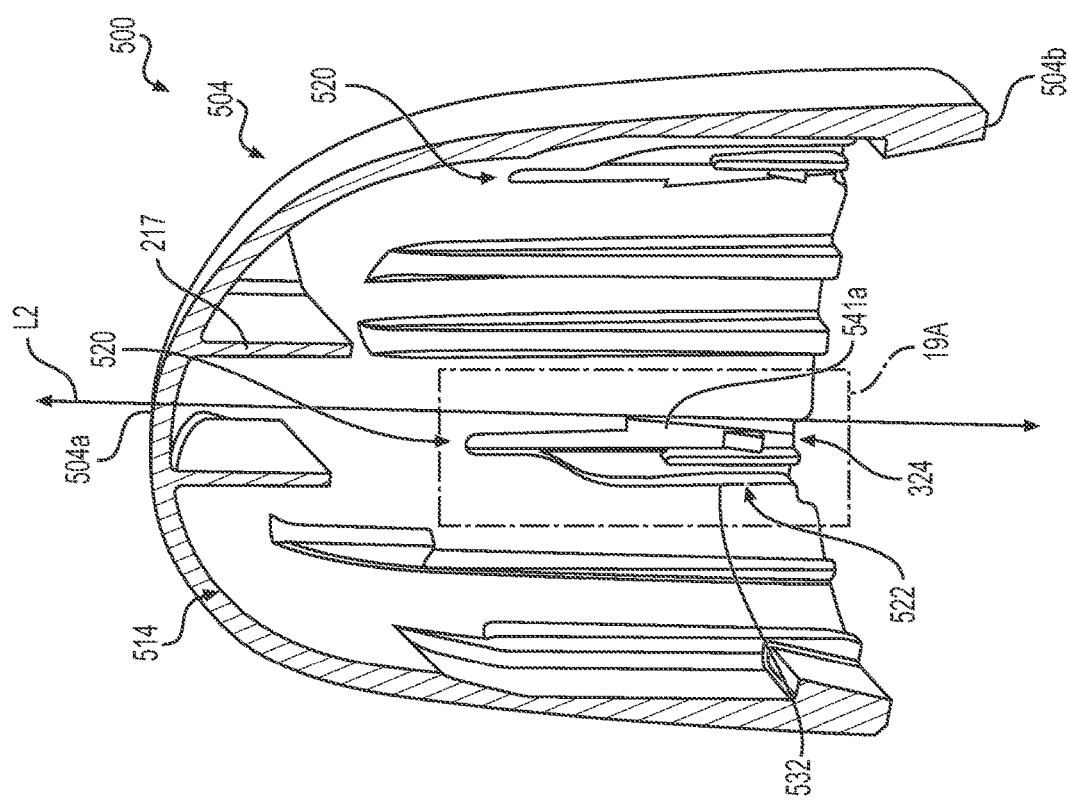
FIG. 19A
FIG. 19

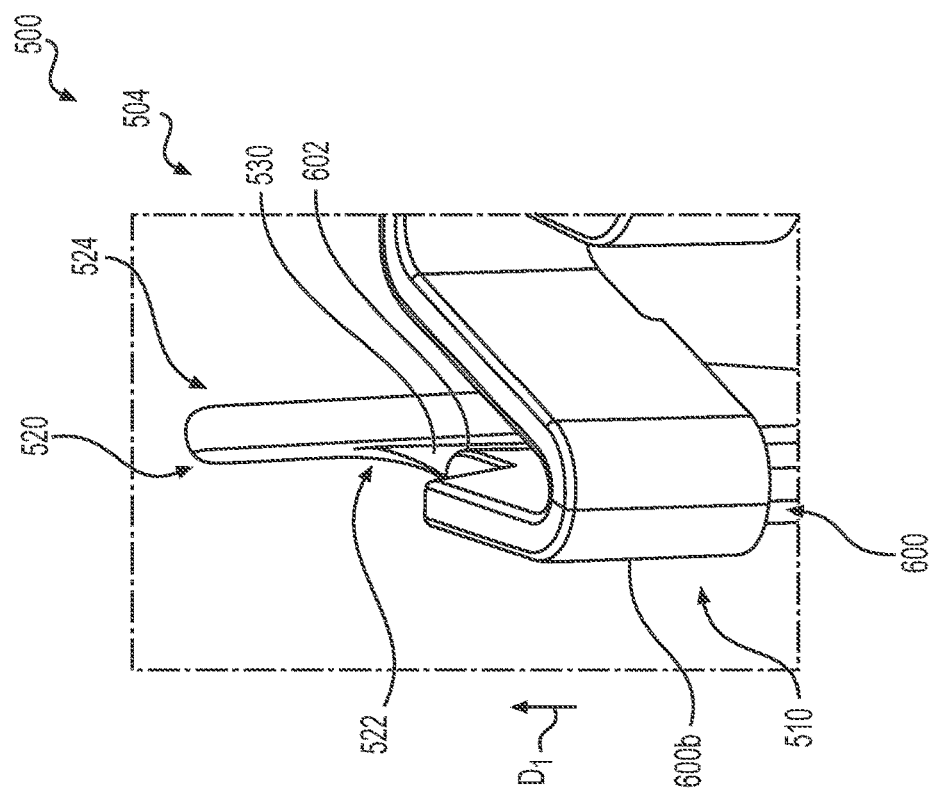
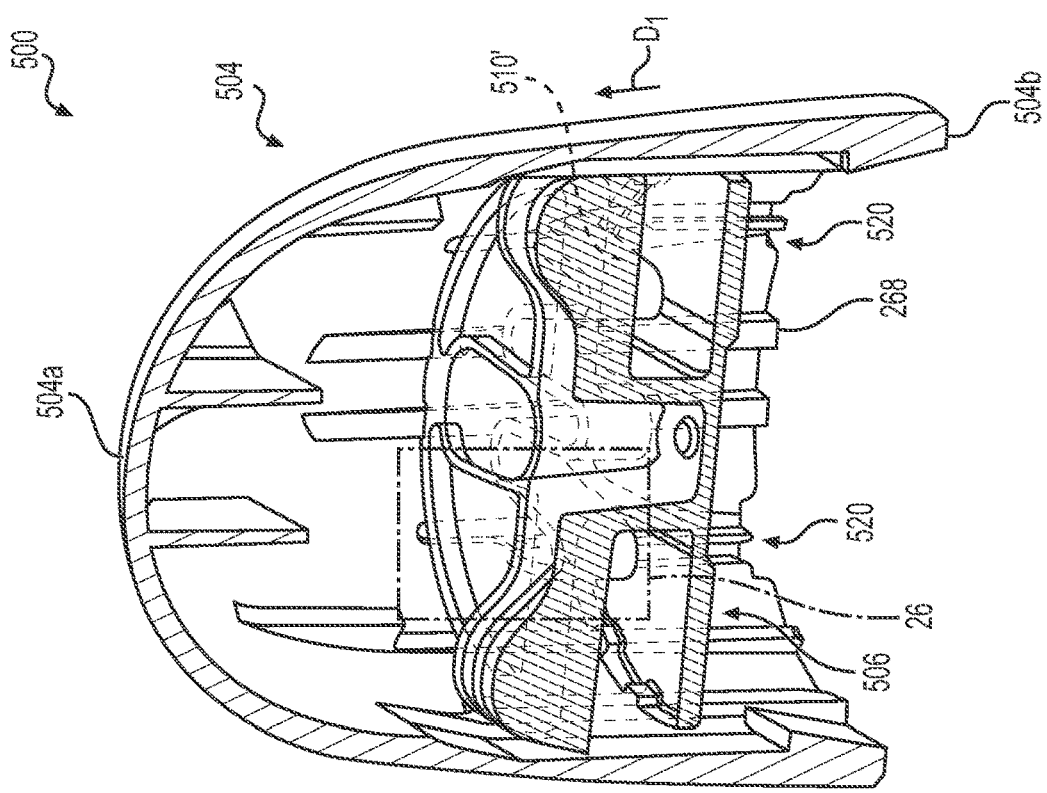
FIG. 26
FIG. 25

SENSOR INSERTER WITH DISPOSAL LOCKOUT STATE

FIELD

Embodiments of the subject matter described herein relate generally to medical devices, such as a sensor inserter for a physiological characteristic sensor assembly. More particularly, embodiments of the subject matter relate to a sensor inserter for coupling the physiological characteristic sensor to a user that has a disposal lockout state that inhibits the further use of the sensor inserter after the physiological characteristic sensor has been coupled to the user. In various embodiments, the physiological characteristic sensor is a glucose sensor.

BACKGROUND

Sensors may be employed in the treatment of or monitoring of various medical conditions. In one example, thin film electrochemical sensors are used to test analyte levels in patients or users. More specifically, thin film sensors have been designed for use in obtaining an indication of blood glucose (BG) levels and monitoring BG levels in a diabetic user, with the distal segment portion of the sensor positioned subcutaneously in direct contact with extracellular fluid. Such readings can be especially useful in adjusting a treatment regimen which typically includes regular administration of insulin to the user.

A glucose sensor of the type described above may be packaged and sold as a product that includes certain features or components that allow the user to position and subcutaneously implant the sensor. For example, thin film glucose sensors are often implanted subcutaneously/transcutaneously using a sensor introducer tool, which may be packaged with the glucose sensor. The sensor introducer contains a needle that is used to puncture the skin of a user at the same time as the sensor is introduced. The needle is then withdrawn, leaving the sensor in the skin of the user.

In certain instances, the sensor inserter is configured to be a one-time use device. This ensures that a desired amount of force is applied each time a sensor is introduced, and may also ensure a sterility of the sensor inserter. In certain instances, however, a user may be tempted to reuse the sensor inserter to introduce a replacement sensor, for example, instead of obtaining a new sensor inserter.

Accordingly, it is desirable to provide a sensor inserter for inserting a physiological characteristic sensor, such as a glucose sensor, which has a disposal lockout state to inhibit the reuse of the sensor inserter. Furthermore, other desirable features and characteristics will become apparent from the subsequent detailed description and the appended claims, taken in conjunction with the accompanying drawings and the foregoing technical field and background.

BRIEF SUMMARY

The techniques of this disclosure generally relate to a sensor inserter that has a disposal lockout state, which inhibits a reuse of the sensor inserter.

According to various embodiments, provided is a sensor inserter for a physiological characteristic sensor. The sensor inserter includes a housing that defines a track system that extends from a bottom of the housing toward a top of the housing. The sensor inserter includes a striker assembly movable relative to the housing between a first state, a second, cocked state and a third, disposal state. The striker assembly is movable from the second, cocked state to the third, disposal state to couple the physiological characteristic sensor to an anatomy. The striker assembly includes a lock beam that engages with the track system as the striker assembly moves between the first state, the second, cocked state and the third, disposal state. In the third, disposal state the lock beam inhibits movement of the striker assembly from the third, disposal state to the first state.

Also provided according to various embodiments is a sensor inserter for a physiological characteristic sensor. The sensor inserter includes a housing that defines a track system that extends from a bottom of the housing toward a top of the housing. The track system includes a first track and a second track. The sensor inserter includes a striker assembly movable relative to the housing between a first state, a second, cocked state and a third, disposal state. The striker assembly is movable from the second, cocked state to the third, disposal state to couple the physiological characteristic sensor to an anatomy. The striker assembly includes a striker that defines a lock beam that engages with the first track or the second track as the striker assembly moves between the first state, the second, cocked state and the third, disposal state. The lock beam extends outwardly from a surface of the striker and includes a tab that engages with the first track and the second track. In the third, disposal state the lock beam inhibits movement of the striker assembly from the third, disposal state to the first state.

Further provided according to various embodiments is a sensor inserter for a physiological characteristic sensor. The sensor inserter includes a housing that defines a track system that extends from a bottom of the housing toward a top of the housing. The track system includes a first track and a second track. The sensor inserter includes a striker assembly movable relative to the housing between a first state, a second, cocked state and a third, disposal state. The striker assembly is movable from the second, cocked state to the third, disposal state to couple the physiological characteristic sensor to an anatomy. The striker assembly includes a striker and a lock beam that engages with the first track or the second track as the striker assembly moves between the first state, the second, cocked state and the third, disposal state. The lock beam is coupled to a channel defined at an end of the striker and includes plurality of undulations and a tab that engages with the track system. In the third, disposal state the lock beam inhibits movement of the striker assembly from the third, disposal state to the first state.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter. The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 3 is a cross-sectional view of a housing of the sensor inserter of FIG. 2, taken along line 3-3 of FIG. 2;

FIG. 3A is a detail view of the housing of FIG. 3, taken at 3 of FIG. 3;

FIG. 3B is a cross-sectional view of the housing of FIG. 3, taken at line 3B-3B of FIG. 3;

FIG. 12 is a cross-sectional view of the sensor inserter of FIG. 1, taken at line 12-12 of FIG. 12A, which illustrates the sensor inserter in the second, cocked state;

FIG. 16 is a cross-sectional view of the sensor inserter of FIG. 1, taken from the perspective of line 12-12 of FIG. 12A, which illustrates the sensor inserter reset from the third, disposal state to the first, shipping state;

FIG. 19 is a cross-sectional view of a housing of the sensor inserter of FIG. 18, taken along line 19-19 of FIG. 18;

FIG. 19A is a detail view of the housing of FIG. 19, taken at 19A of FIG. 19;

FIG. 25 is a cross-sectional view of the sensor inserter of FIG. 17, taken from the perspective of line 21-21 of FIG. 17, which illustrates a lock beam of the sensor inserter at an exit of a first track in accordance with various embodiments;

FIG. 26 is a detail view of the sensor inserter of FIG. 25, taken at 26 of FIG. 25;

DETAILED DESCRIPTION

Figure 1:
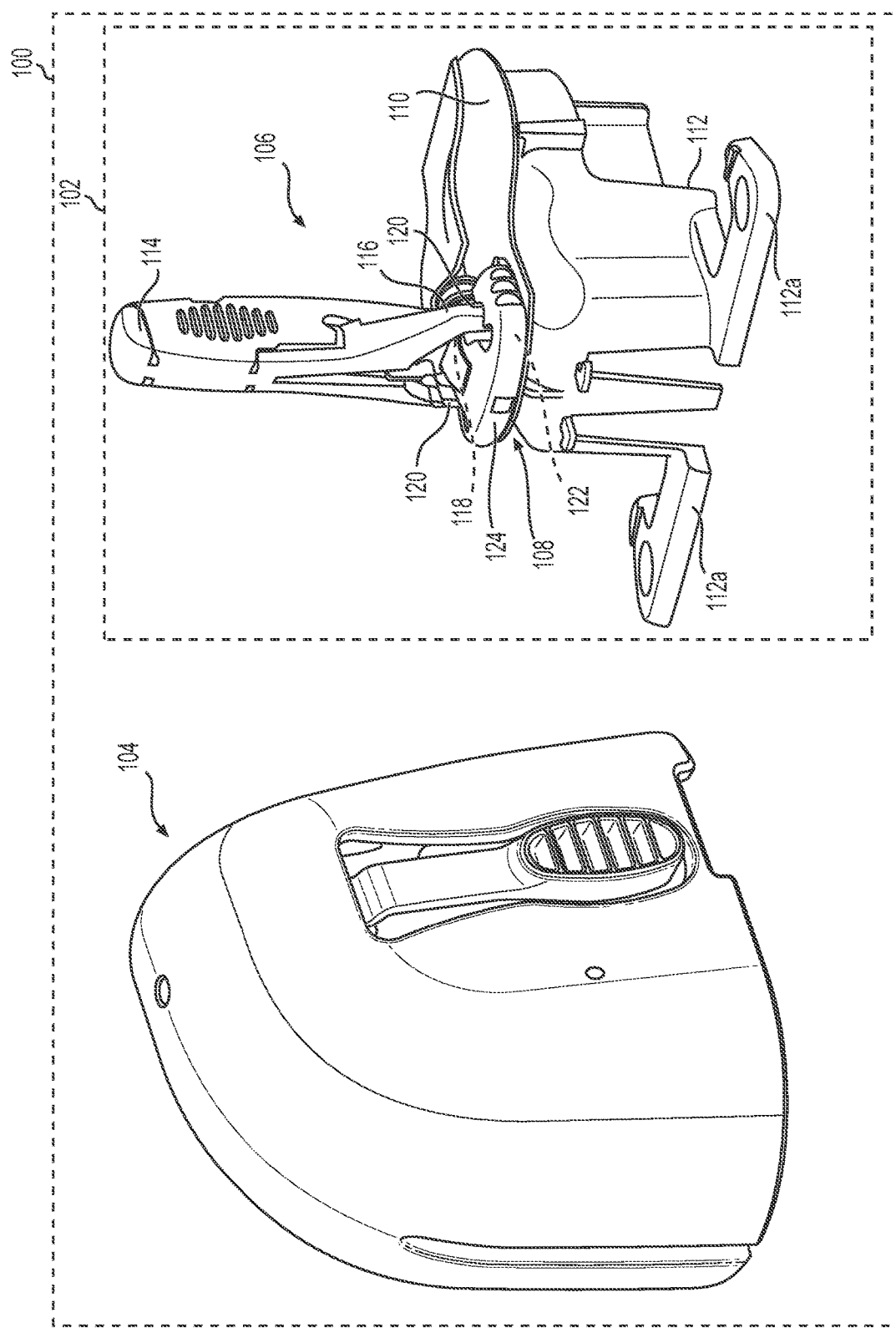
FIG. 1 is a schematic perspective view of an exemplary embodiment of a sensor introduction assembly that includes a sensor inserter with a disposal lockout state according to various teachings of the present disclosure.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominately in the respective nominal axial or radial direction. As used herein, the term "transverse" denotes an axis that crosses another axis at an angle such that the axis and the other axis are neither substantially perpendicular nor substantially parallel.

The following description relates to various embodiments of a sensor inserter. The sensor inserter enables the insertion of a physiological characteristic sensor, such as a glucose sensor, in a cocked state; and in the disposal state, the sensor inserter is inhibited from reuse. This ensures that a new sensor inserter is used to couple a replacement glucose sensor to the user, and eliminates the need for the user to clean and disinfect the sensor inserter as the sensor inserter is a single use component. It should be noted that while the sensor inserter is described herein as being used with a glucose sensor, it will be understood that the sensor inserter may be employed with a variety of other sensors and/or medical devices. Thus, while the non-limiting examples described below relate to a medical device used to treat diabetes (more specifically, a sensor inserter for a glucose sensor), embodiments of the disclosed subject matter are not so limited.

Generally, the glucose sensor employed with the sensor inserter is a continuous glucose sensor of the type used by diabetic users. For the sake of brevity, conventional aspects and technology related to glucose sensors and glucose sensor fabrication may not be described in detail here. In this regard, known and/or conventional aspects of glucose sensors and their manufacturing may be of the type described in, but not limited to: U.S. Pat. Nos. 6,892,085, 7,468,033 and 9,295,786; and U.S. patent application number 2009/0299301 (which are each incorporated by reference herein).

With reference to FIG. 1, FIG. 1 is a perspective view of a sensor introduction assembly 100. In one example, the sensor introduction assembly 100 includes a physiological characteristic sensor assembly 102 and a sensor inserter 104. In one example, the physiological characteristic sensor assembly 102 includes a sensor introducer 106, a physiological characteristic sensor 108, an adhesive patch 110 and a packaging support 112. Generally, the components of the physiological characteristic sensor assembly 102 are coupled together as a single unit for placement in a package tray. It should be noted, however, that the physiological characteristic sensor assembly 102 may be packaged separately from the sensor inserter 104, or the physiological characteristic sensor assembly 102 and the sensor inserter 104 may be packaged together for use by a consumer. As will be discussed further herein, the sensor inserter 104 may be used by a user to remove the sensor introducer 106, the physiological characteristic sensor 108 and the adhesive patch 110 from the packaging support 112, and used to insert the physiological characteristic sensor 108 at a sensor insertion site or sensor site.

Many features, aspects, and characteristics of the physiological characteristic sensor assembly 102 and its individual elements are conventional and, as such, will not be described in detail here. Generally, the sensor introducer 106 is manipulated to introduce a portion of the physiological characteristic sensor 108 into the body of the user. The sensor introducer 106 includes a body having a first end 114 and an opposite second end 116. The first end 114 defines a graspable portion, which enables the user to manipulate the sensor introducer 106 and enables the sensor introducer 106 to be received within and cooperate with the sensor inserter 104. The second end 116 includes an insertion needle 118 and a pair of opposed mating projections 120. Each of the pair of mating projections 120 engage corresponding features on a portion of the physiological characteristic sensor 108 to couple the sensor introducer 106 to the physiological characteristic sensor 108 before introducing a portion of the physiological characteristic sensor 108 into the body of the user.

The sensor introducer 106 and the physiological characteristic sensor 108 can be pre-connected as part of a sensor set, which could also include a sensor electronics module (not shown), such as a wireless transmitter that communicates with an infusion pump, a monitor device, or the like, which connects to the physiological characteristic sensor 108 after the insertion or deployment of a portion of the physiological characteristic sensor 108 in the body of the user. Alternatively, the sensor introducer 106 and the physiological characteristic sensor 108 can be packaged and provided together. In certain embodiments the sensor introducer 106 is composed at least in part from a plastic material. For the embodiment described here, the bulk of the sensor introducer 106 is formed as a molded plastic component. In practice, the sensor introducer 106 may be formed from acrylonitrile butadiene styrene, nylon, an acrylonitrile butadiene styrene polycarbonate blend, polyvinyl chloride, polytetrafluoroethylene (PTFE), polypropylene, polyether ether ketone (PEEK), polycarbonate or the like.

In one example, the physiological characteristic sensor 108 includes a glucose sensor 122 and a sensor base 124. It should be noted that the physiological characteristic sensor 108 is not limited to a glucose sensor, but rather, various other physiological characteristic sensors may be employed. The glucose sensor 122 may be provided as an integral part of the sensor base 124. The sensor base 124 gives structural support to the glucose sensor 122, and facilitates entry of the glucose sensor 122 into the body of the user. The glucose sensor 122 is an electrochemical sensor that includes the glucose oxidase enzyme, as is well understood by those familiar with glucose sensor technology. The glucose oxidase enzyme enables the glucose sensor 122 to monitor blood glucose levels in a diabetic patient or user by effecting a reaction of glucose and oxygen. Again, although certain embodiments pertain to glucose sensors, the manufacturing and packaging technology described here can be adapted for use with any one of the wide variety of sensors known in the art. Generally, the glucose sensor 122 is positionable in subcutaneous tissue of the user by the insertion needle 118 of the sensor introducer 106 to measure the glucose oxidase enzyme.

The sensor base 124 is coupled to the sensor introducer 106 and is coupled to the packaging support 112. The sensor base 124 is removably coupled to the sensor introducer 106 prior to the deployment of the glucose sensor 122 into the subcutaneous tissue of the user. The sensor base 124 is also coupled to the adhesive patch 110. The sensor base 124 may also feature electrical and physical interfaces and elements that accommodate the sensor electronics module (not shown), such as the wireless transmitter that communicates with the infusion pump, the monitor device, or the like. In certain embodiments the sensor base 124 is composed at least in part from a plastic material. For the embodiment described here, the bulk of the sensor base 124 is formed as a molded plastic component. In one example, the sensor base 124 is formed from acrylonitrile butadiene styrene, nylon, an acrylonitrile butadiene styrene polycarbonate blend, polyvinyl chloride, polytetrafluoroethylene (PTFE), polypropylene, polyether ether ketone (PEEK), poly carbonate or the like.

The adhesive patch 110 is coupled to the sensor base 124 and affixes the sensor base 124, and thus, the glucose sensor 122, to the skin of the user. The adhesive patch 110 is retained on, but not secured to, the packaging support 112 during packaging and shipping. The adhesive patch 110 may be composed of a flexible and breathable material with one or more adhesive layers, such as cloth, a bandage-like material, and the like. For example, suitable materials could include polyurethane, polyethylene, polyester, polypropylene, polytetrafluoroethylene (PTFE), or other polymers, to which one or more adhesive layers are applied.

The packaging support 112 receives and protects the insertion needle 118 of the sensor introducer 106 during packaging, shipping, and handling before deployment of the glucose sensor 122. The packaging support 112 also serves to assist a user in the removal of the sensor introducer 106 after the deployment of the glucose sensor 122. In certain embodiments, the packaging support 112 is composed at least in part from a plastic material. For the embodiment described here, the packaging support 112 is formed as a molded plastic component. In one example, the packaging support 112 is formed from acrylonitrile butadiene styrene, nylon, an acrylonitrile butadiene styrene polycarbonate blend, polyvinyl chloride, polytetrafluoroethylene (PTFE), polypropylene, polyether ether ketone (PEEK), polycarbonate or the like. Further detail regarding the manufacture and assembly of the packaging for the physiological characteristic sensor assembly 102 is described in U.S. Pat. No. 9,101,305 to Larson et al., which is incorporated herein by reference.

As will be discussed, the sensor inserter 104 is coupled to the sensor introducer 106 to remove the sensor introducer 106, the physiological characteristic sensor 108 and the adhesive patch 110 from the packaging support 112 to couple the glucose sensor 122 to the user. In one example, the sensor inserter 104 is sized to be positioned over at least the sensor introducer 106 and the physiological characteristic sensor 108.

Figure 2:
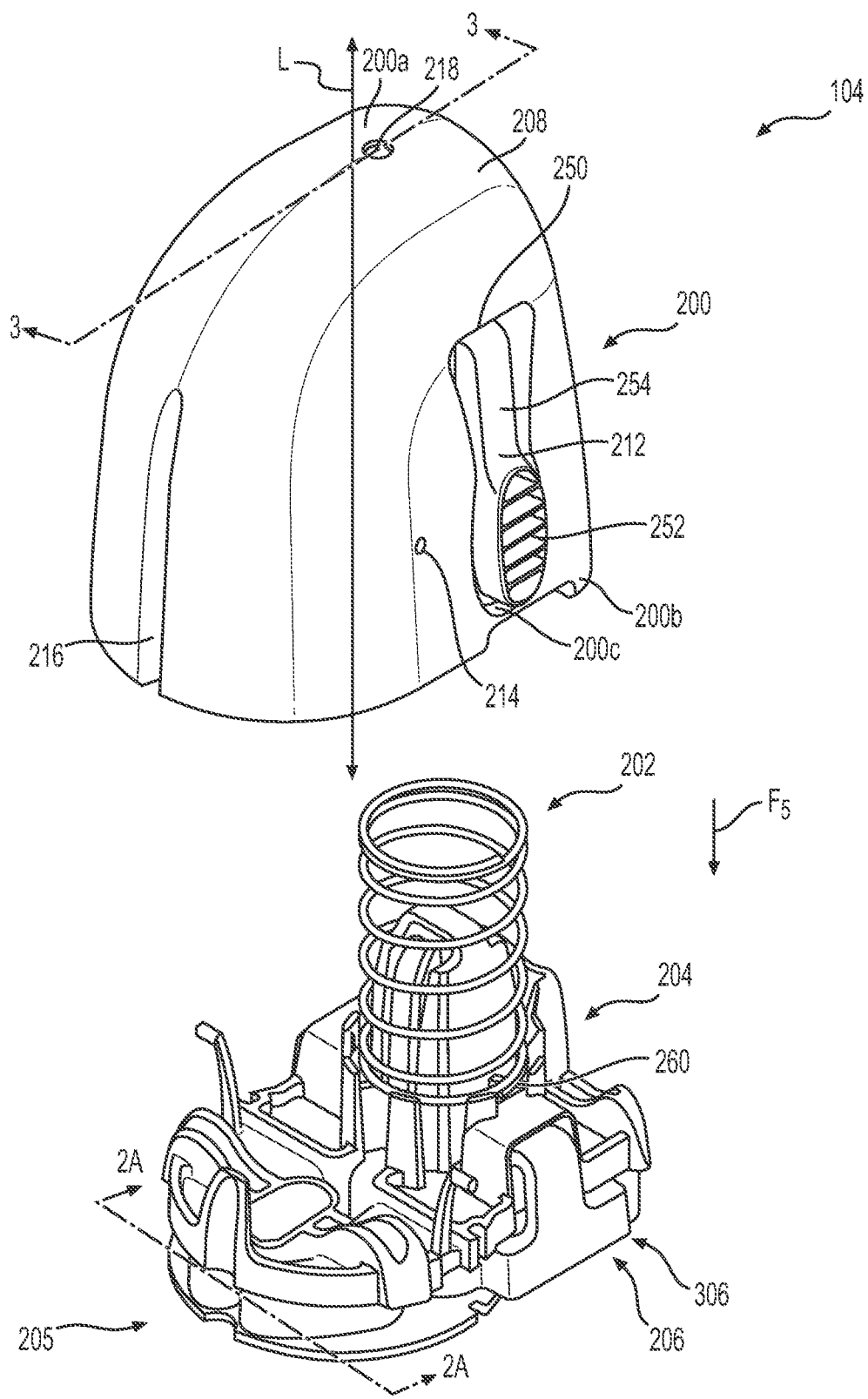
FIG. 2 is a partially exploded view of the sensor inserter of FIG. 1.

With reference to FIG. 2, a partially exploded view of the sensor inserter 104 is shown. The sensor inserter 104 includes a housing 200, a biasing member or spring 202, a striker 204 and a release body 206. The striker 204 and the release body 206 form a striker assembly 205. The housing 200 is substantially U-shaped, and receives the spring 202, the striker 204 and the release body 206. The housing 200 is generally symmetric with respect to a longitudinal axis L, which extends through the housing 200. The housing 200 is composed of a polymer-based material, including, but not limited to acrylonitrile butadiene styrene, polyoxymethylene, polyamide, polyethylene, polypropylene, polyvinyl chloride, polycarbonate, or the like. The housing 200 may be formed by injection molding, casting, etc. The housing 200 includes an outer surface 208 opposite an inner surface 210 (FIG. 3), a pair of biasing tabs 212, a pair of reset passages or bores 214, a pair of notches 216 and a spring guide 217 (FIG. 3). The housing 200 also includes a first, top surface 200a opposite a second, bottom surface 200b. The bottom surface 200b is circumferentially open to enable the spring 202, the striker 204 and the release body 206 to be received within the housing 200, and for the housing 200 to be positioned over at least the sensor introducer 106 and the physiological characteristic sensor 108. Thus, the bottom surface 220b defines a bore, through which the spring 202, the striker 204 and the release body 206 are received within the housing 200, and that enables the housing 200 to be positioned over at least the sensor introducer 106 and the physiological characteristic sensor 108. The outer surface 208 may include a depression 218. The depression 218 may be defined on the top surface 200a of the housing 200, and may assist in the forming of the housing 200.

With reference to FIG. 3, a cross-section of the housing 200 is shown. As shown in FIG. 3, the inner surface 210 defines at least one track system 220. In this example, the inner surface 210 defines two opposed track systems 220, one on each side of the housing 200. The track systems 220 cooperate with a portion of the striker 204 to move the sensor inserter 104 between a first, shipping state to a second, cocked state and from the second, cocked state to a third, disposal state. As the track systems 220 are the same and symmetric with respect to the longitudinal axis L, a single one of the track systems 220 will be described herein. In this example, the track system 220 is defined on the inner surface 210 between one of the pair of biasing tabs 212 and one of the notches 216. Generally, the track system 220 is defined as a recess on the inner surface 210 that does not extend to the outer surface 208 (FIG. 2). In one example, the track system 220 includes a first track 222 and a second track 224.

The first track 222 extends from the bottom surface 200b of the housing 200 toward the top surface 200a. The first track 222 guides the portion of the striker 204 as the sensor inserter 104 moves from the first, shipping state to the second, cocked state. With reference to FIG. 3A, the first track 222 includes an entrance 226, an intermediate track portion 228 and an exit 230. The entrance 226 is defined at the bottom surface 220b, and may taper from a first diameter at the bottom surface 220b to a smaller, second diameter at the intermediate track portion 228. The intermediate track portion 228 extends from the entrance 226 to the exit 230. The intermediate track portion 228 includes a sloped surface 232, which guides the portion of the striker 204 in a direction F, or a direction toward one of the notches 216. The exit 230 is in communication with the second track 224. The exit 230 has a curved surface 234, which assists in directing the portion of the striker 204 into the second track 224. The curved surface 234 extends a distance outward from the inner surface 210 to ensure that the portion of the striker 204 remains within the first track 222 and transitions into the second track 224 at the exit 230.

Generally, with reference to FIG. 3B, the first track 222 is defined at a first depth DT1, which is different than a second depth DT2 of the second track 224. In one example, the first depth DT1 is less than the second depth DT2, such that once the portion of the striker 204 has entered the second track 224, a first step 236 is defined between the first depth DT1 and the second depth DT2 that retains the portion of the striker 204 within the second track 224. In one example, the first step 236 has a thickness ST of about 0.5 millimeters (mm) to about 1.5 millimeters (mm). With reference back to FIG. 3A, the first track 222 generally extends along a first axis A1 and the second track 224 extends along a second axis A2. The first axis A1 and the second axis A2 are substantially parallel, and are substantially parallel to the longitudinal axis L (FIG. 3).

The second track 224 extends from near the top surface 200a to the respective reset bore 214. The second track 224 guides the portion of the striker 204 as the sensor inserter 104 moves from the second, cocked state to the third, disposal state. The second track 224 includes a second entrance 240, a ramp 242 and a second exit 243. The second entrance 240 is in communication with the exit 230 of the first track 222. The second entrance 240 extends for a distance 246 along the longitudinal axis L that is beyond the exit 230 to enable a movement of the striker 204 to the second, cocked state prior to entering the third, disposal state. The ramp 242 guides the portion of the striker 204 from the second, cocked state to the third, disposal state. The ramp 242 interconnects the second entrance 240 and the second exit 243. The ramp 242 is inclined relative to the second entrance 240 with a positive slope (FIG. 3B), which causes a compression of the portion of the striker 204 such that once the portion of the striker 204 moves beyond the ramp 242, the portion of the striker 204 expands into the second exit 243. Generally, a wall 248 that separates the first track 222 from the second track 224 extends for a distance from the inner surface 210 to ensure that the portion of the striker 204 remains within the second track 224 as the portion of the striker 204 moves down the ramp 242. The incline of the ramp 242 also inhibits the portion of the striker 204 from moving up and back over the ramp 242 by defining a second step 242a. The second step 242a is generally planar, and inhibits the retraction or rearward movement of the portion of the striker 204 once the portion of the striker 204 has moved over the ramp 242. Thus, the second step 242a cooperates with the lock beam 274 to inhibit reusing of the sensor inserter 104. The second exit 243 is proximate the respective reset bore 214. The sensor inserter 104 is in the third, disposal state when the portion of the striker 204 is received within the second exit 243 and is proximate the reset bore 214.

The inner surface 210 also defines a pair of stops 244 for the release body 206. The stops 244 are defined on opposed sides of the housing 200, and in one example, are each defined proximate a respective one of the pair of biasing tabs 212. In this example, each of the stops 244 are defined on opposed sides of the respective biasing tab 212 such that each of the stops 244 includes a first stop surface 244a and a second stop surface 244b, with the stop surfaces 244a, 244b being spaced apart by the biasing tab 212. The stops 244 receive and support the release body 206, and thus, the striker 204, in the second, cocked state, and the striker 204 may be released from the stops 244 by the user manipulating the biasing tabs 212.

With reference back to FIG. 2, the pair of biasing tabs 212 are identical and symmetric with respect to the longitudinal axis L. As the biasing tabs 212 are the same, a single one of the biasing tabs 212 will be discussed herein. The biasing tab 212 includes a hinge 250, a graspable portion 252 and an arm 254. In one example, the hinge 250 is a living hinge, which is formed at the interconnection of the arm 254 with the housing 200. The hinge 250 enables the graspable portion 252 to move relative to the housing 200. The housing 200 may include a pair of cut-out regions 200c, which enables the movement of the biasing tabs 212 relative to the housing 200. The graspable portion 252 provides a surface for the user to manipulate to move the biasing tab 212 relative to the housing 200. Generally, the graspable portion 252 is manipulated by the user by squeezing the biasing tabs 212 inward toward each other to insert the glucose sensor 122 (FIG. 1) into the anatomy. In one example, the graspable portion 252 is pushed inward by the user to release the striker 204 for coupling the glucose sensor 122 to the anatomy. The arm 254 interconnects the graspable portion 252 and the hinge 250. The arm 254 cantilevers the graspable portion 252 relative to the hinge 250.

The reset bores 214 are defined on opposite sides of the housing 200, and each of the reset bores 214 receive a special tool to move the portion of the striker 204 to reset the sensor inserter 104 from the third, disposal state to the first, shipping state. Generally, the reset bores 214 have a diameter that is sized such that the special tool may be used to release the portion of the striker 204 during manufacture, for example, to ensure the sensor inserter 104 is functioning appropriately. In one example, the reset bores 214 have a diameter of about 0.5 millimeters (mm) to about 2.0 millimeters (mm). Thus, the reset bores 214 are sized such that the reset bores 214 are not able to be used by a consumer to reset the sensor inserter 104.

The pair of notches 216 are each defined along an end of the housing 200 from the bottom surface 200b toward the top surface 200a. The pair of notches 216 are defined on opposed ends of the housing 200, and cooperate with the striker 204 to guide a movement of the striker 204 within and relative to the housing 200. The notches 216 generally extend inward to form rails, which cooperate with corresponding features on the striker 204.

With reference to FIG. 3, the spring guide 217 is defined to extend inwardly from the top surface 200a toward the bottom surface 200b. In one example, the spring guide 217 is defined at the top surface 200a to be proximate or near the biasing tabs 212. The spring guide 217 acts as a spring seat, and maintains a position of the spring 202 within the housing 200.

With reference back to FIG. 2, the spring 202 biases the striker 204 from the second, cocked state to the third, disposal state. In one example, the spring 202 is a coiled compression spring, which is composed of a spring steel. The spring 202 applies a spring force Fs to the striker 204 to move the striker 204 from near the top surface 200a of the housing 200 (in the second, cocked state) to the third, disposal state. An end of the spring 202 is positioned about the spring guide 217 (FIG. 3) and an opposing end of the spring 202 is positioned about a spring seat 260 of the striker 204.

Figure 5B:
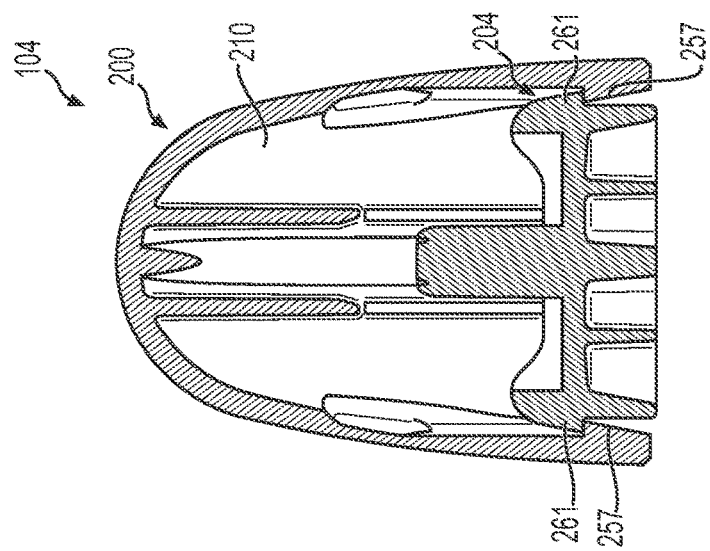
FIG. 5B is a cross-sectional view of the sensor inserter of FIG. 1, taken along line 5B-5B of FIG. 5.
Figure 5A:
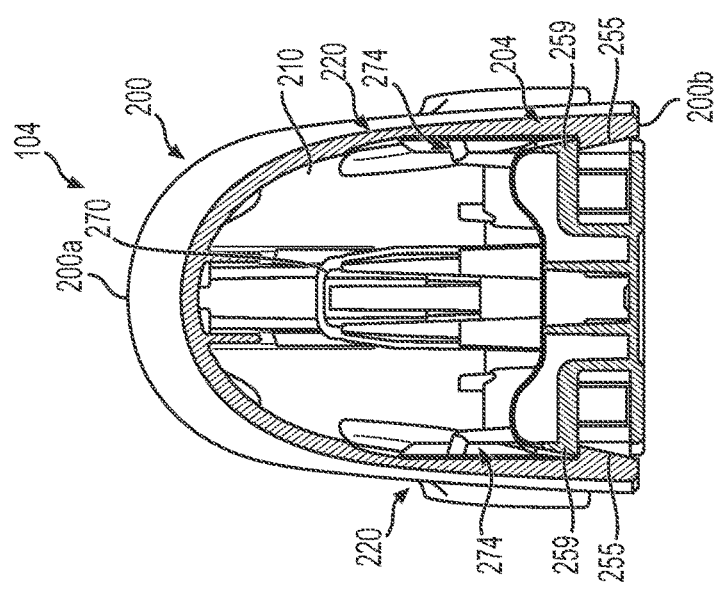
FIG. 5A is a cross-sectional view of the sensor inserter of FIG. 1, taken along line 5A-5A of FIG. 5.

With brief reference to FIGS. 5A and 5B, a cross-section through the housing 200 and the striker 204 is shown. In FIGS. 5A and 5B, the spring 202 is removed for clarity. In this example, the housing 200 includes a pair of first retention catches 255 (FIG. 5A) and a pair of second retention catches 257 (FIG. 5B). The first retention catches 255 (FIG. 5A) and the second retention catches 257 (FIG. 5B) project outward from the inner surface 210. The striker 204 includes a pair of first retention snaps 259 (FIG. 5A) and a pair of second retention snaps 261 (FIG. 5B). The first retention snaps 259 (FIG. 5A) and the second retention snaps 261 (FIG. 5B) project outwardly from the striker 204. The first retention catches 255 (FIG. 5A) cooperate with the first retention snaps 259 (FIG. 5A) and the second retention catches 257 (FIG. 5B) cooperate with the second retention snaps 261 (FIG. 5B) to couple the striker 204 to the housing 200 such that the striker 204 is retained within the housing 200. Generally, the first retention catches 255 (FIG. 5A), first retention snaps 259, the second retention catches 257 (FIG. 5B) and the second retention snaps 261 (FIG. 5B) form a snap-fit that enables the assembly of the striker 204 to the housing 200.

The striker 204 is movable relative to the housing 200 to couple the glucose sensor 122 (FIG. 1) to the user. In one example, with reference to FIG. 4, the striker 204 includes a first end 262 opposite a second end 264, a top striker surface 266 opposite a bottom striker surface 268, a sensor introducer receiving portion 270, a release receiving channel 272 and a pair of lock beams 274. The striker 204 is composed of a polymer-based material, including, but not limited to acrylonitrile butadiene styrene, polyoxymethylene, polyamide, polyethylene, polypropylene, polyvinyl chloride, polycarbonate, or the like. The striker 204 may be formed by injection molding, casting, etc. The striker 204 is symmetric with respect to the longitudinal axis L.

The first end 262 of the striker 204 includes a notch 278, which receives one of the notches 216 of the housing 200.

The notch 278 cooperates with the one of the notches 216 to guide the movement of the striker 204 within the housing 200. With reference to FIG. 5, the second end 264 includes a second notch 280, which receives the other one of the notches 216 of the housing 200. The second notch 280 cooperates with the other one of the notches 216 to guide the movement of the striker 204 within the housing 200. With reference back to FIG. 4, the top striker surface 266 defines the spring seat 260. In one example, the spring seat 260 is defined about a perimeter of the sensor introducer receiving portion 270, which extends axially from the top striker surface 266.

Figure 5:
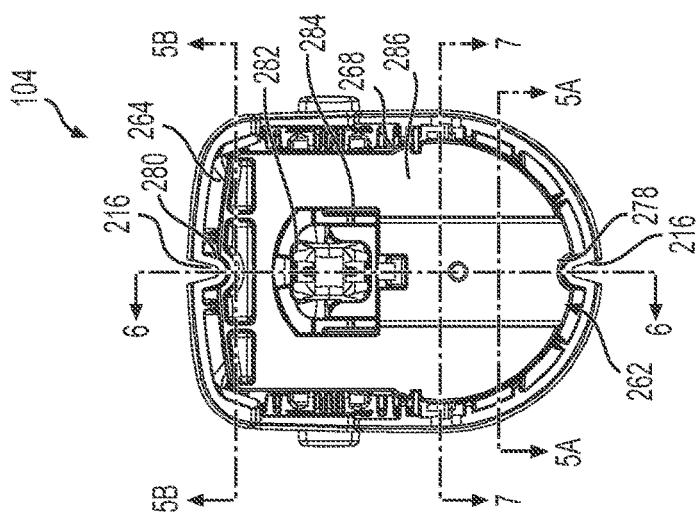
FIG. 5 is an end view of the sensor inserter of FIG. 1.
Figure 5D:
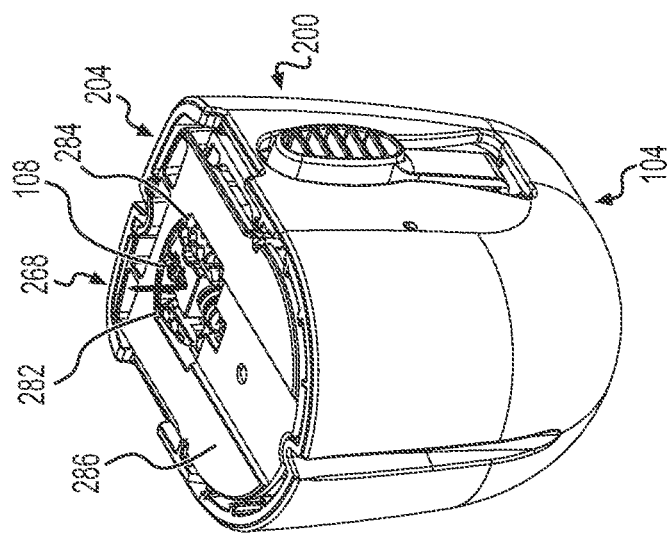
FIG. 5D is an end view of the sensor inserter of FIG. 1, in which the physiological characteristic sensor assembly is coupled to the sensor inserter and an adhesive patch is removed from the physiological characteristic sensor assembly for clarity.
Figure 5C:
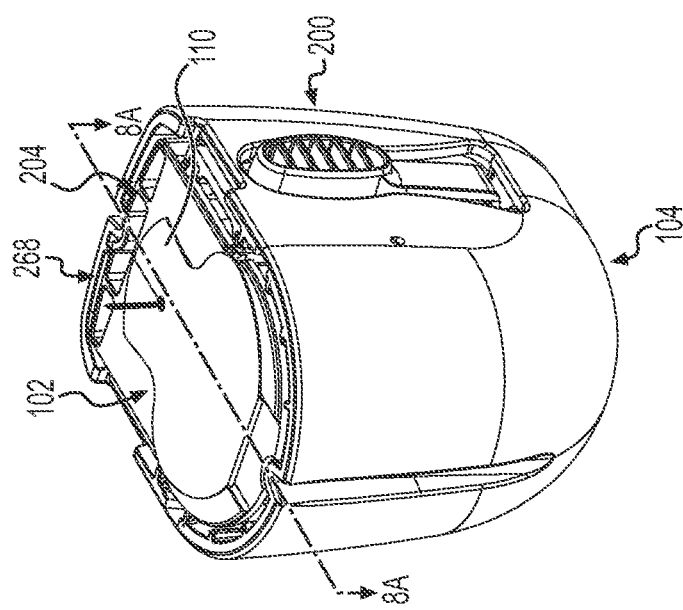
FIG. 5C is an end view of the sensor inserter of FIG. 1, in which a physiological characteristic sensor assembly is coupled to the sensor inserter.

With reference to FIG. 5C, the bottom striker surface 268 receives the sensor introducer 106, the physiological characteristic sensor 108 and the adhesive patch 110 to couple the sensor introducer 106, the physiological characteristic sensor 108 and the adhesive patch 110 to the sensor inserter 104. In this example, with reference to FIG. 5D, the bottom striker surface 268 defines a bore 282, a sensor receiving surface 284 and a patch receiving surface 286. With reference to FIG. 5, the bore 282 is in communication with the sensor introducer receiving portion 270, and enables the sensor introducer 106 to be received within the sensor inserter 104. The bore 282 has a shape, which corresponds to a shape of the sensor introducer 106 (FIG. 1). In this example, the bore 282 is substantially oval, however, the bore 282 may have any desired shape. The sensor receiving surface 284 is defined about the bore 282, and is shaped to correspond with a shape of the physiological characteristic sensor 108 (FIG. 1). In this example, the sensor receiving surface 284 is substantially rectangular, however, the sensor receiving surface 284 may have any desired shape. The patch receiving surface 286 is defined about the sensor receiving surface 284 and the bore 282. The patch receiving surface 286 is shaped to correspond with a shape of the adhesive patch 110 (FIG. 1). In this example, the patch receiving surface 286 is substantially rectangular, however, the patch receiving surface 286 may have any desired shape.

Figure 6:
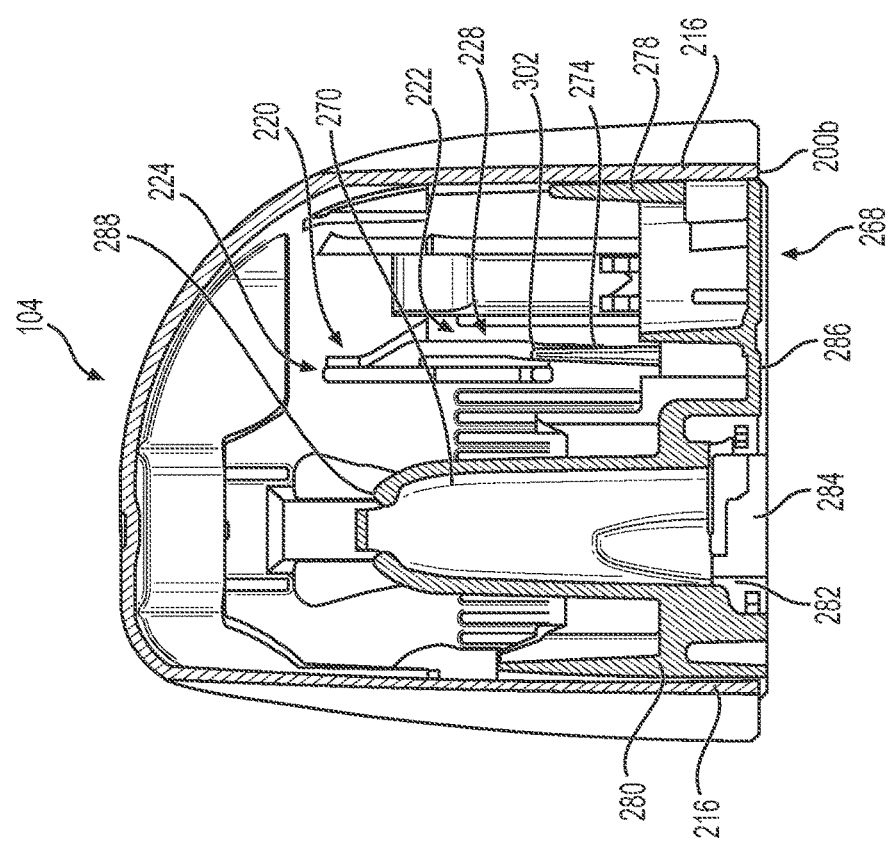
FIG. 6 is a cross-sectional view of the sensor inserter of FIG. 1, taken along line 6-6 of FIG. 5, which illustrates the sensor inserter in a first, shipping state.

With reference to FIG. 6, the sensor introducer receiving portion 270 extends from the top striker surface 266 and is in communication with the bore 282. The sensor introducer receiving portion 270 generally defines a substantially enclosed chamber for receiving the sensor introducer 106. The sensor introducer receiving portion 270 may have a shape that corresponds with a shape of the sensor introducer 106 (FIG. 1), and in this example, the sensor introducer receiving portion 270 has a substantially rectangular shape that is tapered proximate a terminal end 288. It should be noted, however, that sensor introducer receiving portion 270 may have any desired shape. As will be discussed, the sensor introducer receiving portion 270 cooperates with the sensor introducer 106 such that as the sensor introducer 106 is received within the sensor introducer receiving portion 270, the sensor introducer 106 moves the striker 204 relative to the housing 200.

Figure 4:
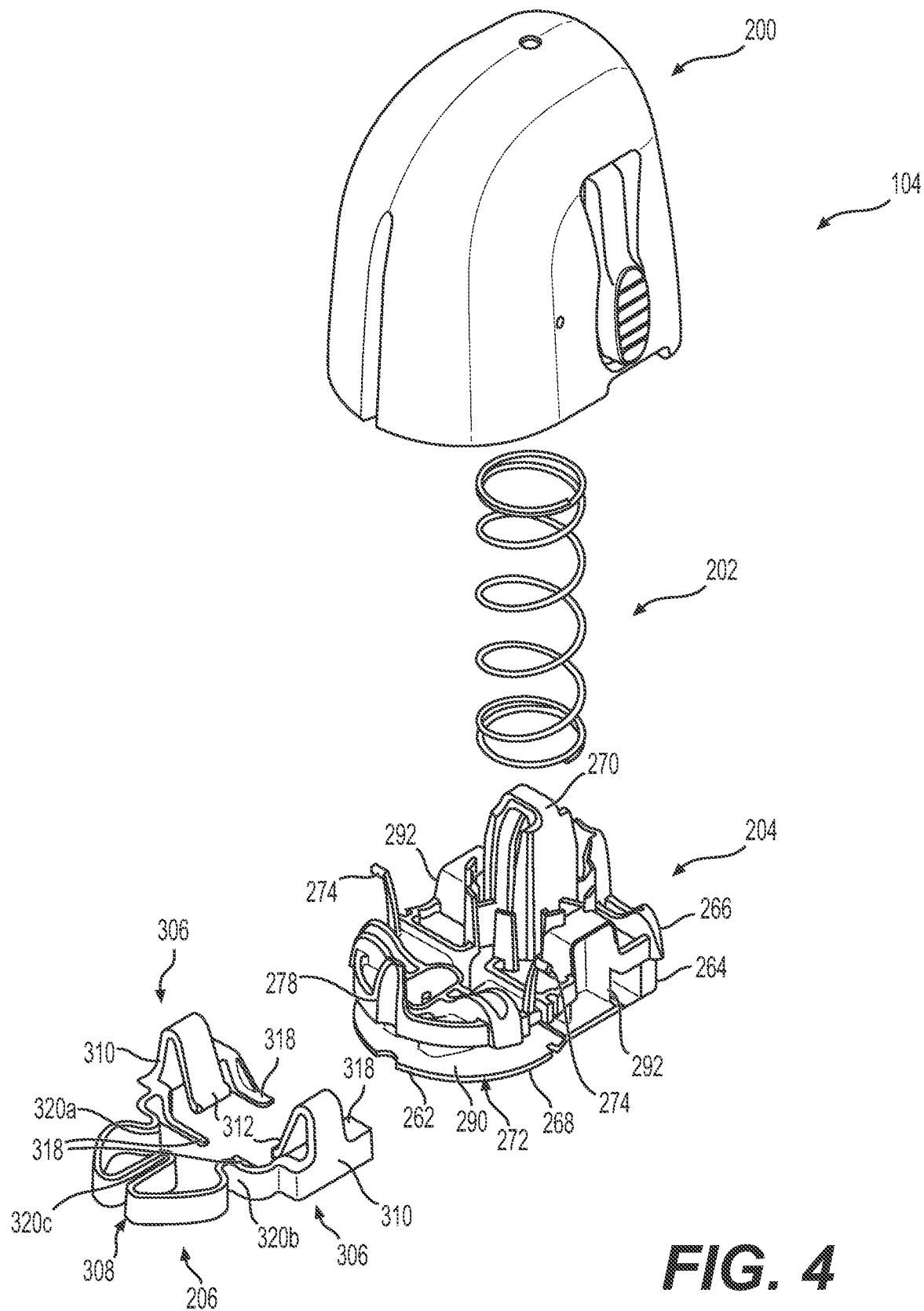
FIG. 4 is an exploded view of the sensor inserter of FIG. 1.

With reference to FIG. 4, the release receiving channel 272 receives the release body 206. The release receiving channel 272 generally defines a curved channel 290 along a perimeter of the striker 204 that terminates in opposed pockets 292. The pockets 292 each receive a portion of the release body 206 that is movable relative to the striker 204 to enable the striker 204 to move from the second, cocked state to the third, disposal state. The pockets 292 are each defined proximate the second end 264.

Figure 7:
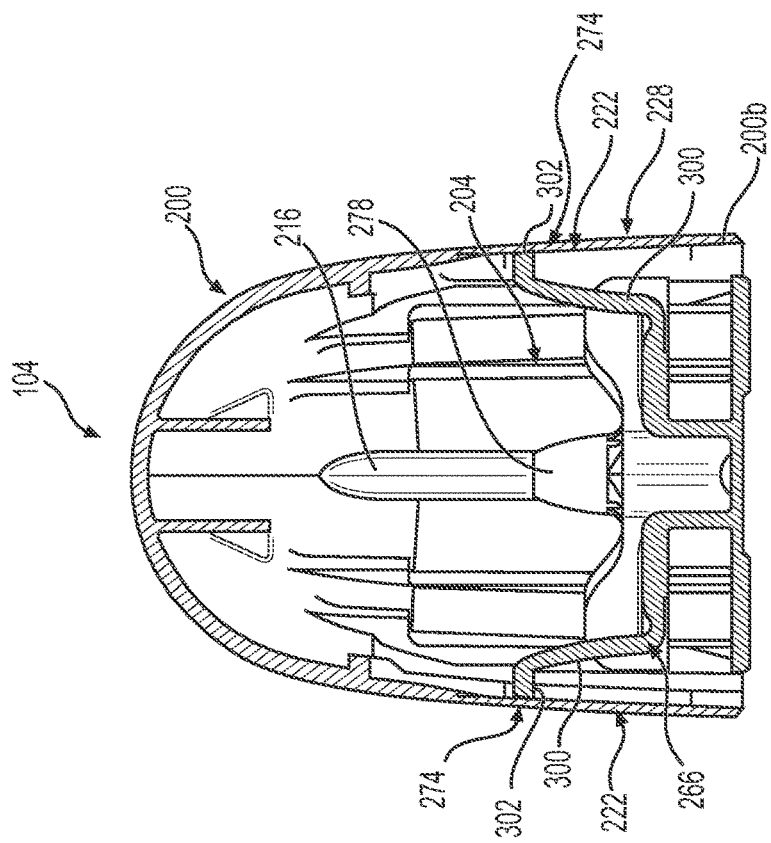
FIG. 7 is a cross-sectional view of the sensor inserter of FIG. 1, taken along line 7-7 of FIG. 5, which illustrates the sensor inserter in the first, shipping state.

The lock beams 274 extend outwardly from the top striker surface 266. The lock beams 274 are on opposed sides of the striker 204. With reference to FIG. 7, the lock beams 274 engage with the track system 220 of the housing 200. Each of the lock beams 274 includes a body 300 and a tab 302. The body 300 is coupled to the top striker surface 266, and has a curvature. The curvature of the body 300 ensures that the tab 302 engages with the track system 220 as the striker 204 moves relative to the housing 200. The tab 302 is cylindrical, and extends from the body 300 to engage with the track system 220. The tab 302 is cantilevered from the striker 204 by the body 300. By cantilevering the tab 302 with the body 300, the lock beams 274 are able to be biased or compressed toward the striker 204 when the tab 302 is engaged with the second track 224, and are relaxed or uncompressed when the tab 302 is engaged with the first track 222. Thus, the lock beams 274 are movable relative to the striker 204 as the lock beams 274 transition from the first track 222 to the second track 224.

With reference back to FIG. 4, the release body 206 is movable to release the striker 204 from the second, cocked state to enable the striker 204 to move to the third, disposal state. The release body 206 is symmetric with respect to the longitudinal axis L, and is composed of a polymer-based material, including, but not limited to acrylonitrile butadiene styrene, polyoxymethylene, polyamide, polyethylene, polypropylene, polyvinyl chloride, polycarbonate, or the like. The release body 206 may be formed by injection molding, casting, etc. The release body 206 defines a pair of release tabs 306 that are interconnected by an intermediate portion 308.

The pair of release tabs 306 include a contact portion 310 and a biasing portion 312. Generally, the release tabs 306 are movable relative to the striker 204 and the housing 200 between an expanded state and a compressed state. The contact portion 310 is sized to be contacted by a respective one of the biasing tabs 212 when the user manipulates the biasing tabs 212 into the housing 200. The contact portion 310 also contacts the stops 244 of the housing 200 to retain the striker 204 in the second, cocked state. The biasing portion 312 is received into a respective one of the pockets 292 of the striker 204, and is movable to engage or disengage the contact portion 310 with the stops 244 of the housing 200. The biasing portion 312 is coupled to the contact portion 310 by a hinge, and is compressible into the compressed state by the application of a force by the user's manipulation of the biasing tabs 212 to disengage the contact portion 310 with the stops 244 to move the striker 204 to the third, disposal state.

Generally, in the first, shipping state, the biasing portion 312 is compressed into the compressed state by one or more ribs 314 of the inner surface 210 of the housing 200 (FIG. 3), such that upon a movement of the striker 204 to the second, cocked state, the biasing portion 312 expands into the expanded state and the contact portion 310 rests upon the stops 244. Stated another way, with brief reference to FIG. 3, the ribs 314 extend outwardly from the inner surface 210 for a distance greater than a distance of one or more ribs 316 of the inner surface 210 that are proximate the stops 244. With reference back to FIG. 4, this enables the biasing portion 312 to expand and the contact portion 310 to engage the stops 244 in the expanded state. A pair of projecting legs 318 may extend inward toward the opposing release tab 306 from either side of the respective release tabs 306 to guide the movement of the respective release tab 306 and to inhibit twisting of the release tab 306, for example, as the release tab 306 is compressed into the compressed state.

The intermediate portion 308 interconnects the release tabs 306, and is flexible to enable the movement of the release tabs 306 between the expanded state (where the release tabs 306 are engaged with the stops 244 of the housing 200) and the compressed state (where the release tabs 306 are released from the stops 244 of the housing 200). In one example, the intermediate portion 308 includes a plurality of bends 320a-320c, which cooperate to enable the release tabs 306 to move relative to the release body 206. The bends 320a, 320b are defined proximate a respective one of the release tabs 306 to enable the release tabs 306 to deflect inward into the compressed state. The bend 320c is defined between the bends 320a, 320b and is connected to the bends 320a, 320b by arcuate portions. The bend 320c enables the opposed sides of the release body 206 to flex, if needed, during a movement of the release tabs 306.

Figure 2A:
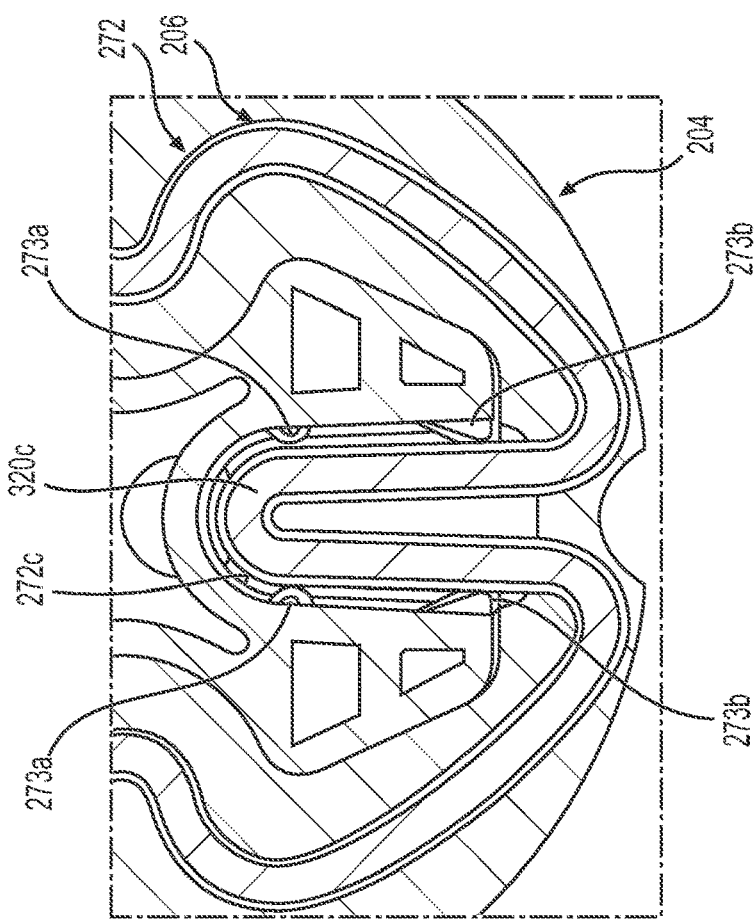
FIG. 2A is a cross-sectional view of the sensor inserter of FIG. 1, taken along line 2A-2A of FIG. 2, which shows a release body coupled to a striker of the sensor inserter.
Figure 2B:
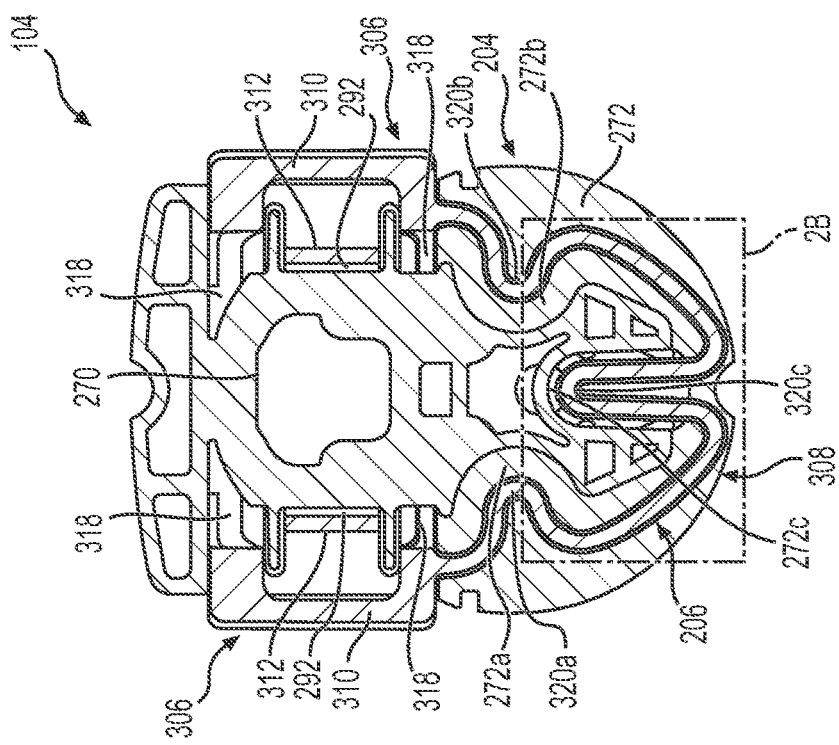
FIG. 2B is a detail view of the release body and the striker of FIG. 3, taken at 2B of FIG. 2A.

The intermediate portion 308 is received within the release receiving channel 272 of the striker 204. In one example, with reference to FIG. 2A, the bend 320a is received within a first curved portion 272a of the release receiving channel 272 and the bend 320b is received within a second curved portion 272b of the release receiving channel 272. The bend 320c is received within a third curved portion 272c of the release receiving channel 272. In this example, with reference to FIG. 2B, the third curved portion 272c of the release receiving channel 272 includes one or more projections 273. The projections 273 extend outwardly from the release receiving channel 272 to contact the intermediate portion 308. The contact between the projections 273 and the intermediate portion 308 cooperate to retain the release body 206 within the striker 204. It should be noted that two of the projections 273a, 273a have a rounded shape, while two of the projections 273b, 273b have a wedge shape. It should be noted that the projections 273 may have any desired shape to retain the release body 206 within the striker 204.

In one example, in order to assemble the sensor inserter 104, with the housing 200, the striker 204 and the release body 206 formed, the release body 206 is coupled to the release receiving channel 272 of the striker 204. In one example, the release body 206 is coupled to the striker 204 with a snap-fit. The spring 202 is coupled to the striker 204 so as to be positioned about the sensor introducer receiving portion 270. The housing 200 is coupled to the striker 204. In one example, the housing 200 is coupled to the striker 204 with a snap-fit via the interaction between the first retention catches 255 (FIG. 5A) and the first retention snaps 259 (FIG. 5A); and the second retention catches 257 (FIG. 5B) and the second retention snaps 261.

With the sensor inserter 104 assembled, the sensor inserter 104 may be used to couple the glucose sensor 122 (FIG. 1) to an anatomy of a user. In one example, with reference to FIGS. 6 and 7, the sensor inserter 104 is in the first, shipping state. In FIGS. 6 and 7, the spring 202 and the release body 206 have been removed for clarity. In the first, shipping state, the sensor introducer receiving portion 270 is spaced apart from the top surface 200a of the housing 200, and the bottom striker surface 268 extends slightly beyond the bottom surface 200b of the housing 200. In the first, shipping state, the tab 302 is engaged with the intermediate track portion 228 of the first track 222. In the first, shipping state, the sensor inserter 104 may be packaged, in suitable packaging, for receipt by the consumer or user.

With brief reference to FIG. 1, with the sensor introducer 106, the glucose sensor 122, the sensor base 124, the adhesive patch 110 and the packaging support 112 formed, the physiological characteristic sensor assembly 102 may be assembled. In one example, the glucose sensor 122 is coupled to the sensor base 124, and this assembly is coupled to the adhesive patch 110. The adhesive patch 110 is coupled to the packaging support 112. The sensor introducer 106 is coupled to the sensor base 124 by inserting the mating projections 120 into the sensor base 124. Once assembled, the physiological characteristic sensor assembly 102 may be packaged, in suitable packaging, for receipt by the consumer or user. Once received by the consumer or user, the sensor inserter 104 and the physiological characteristic sensor assembly 102 may be removed from the packaging.

Figure 8A:
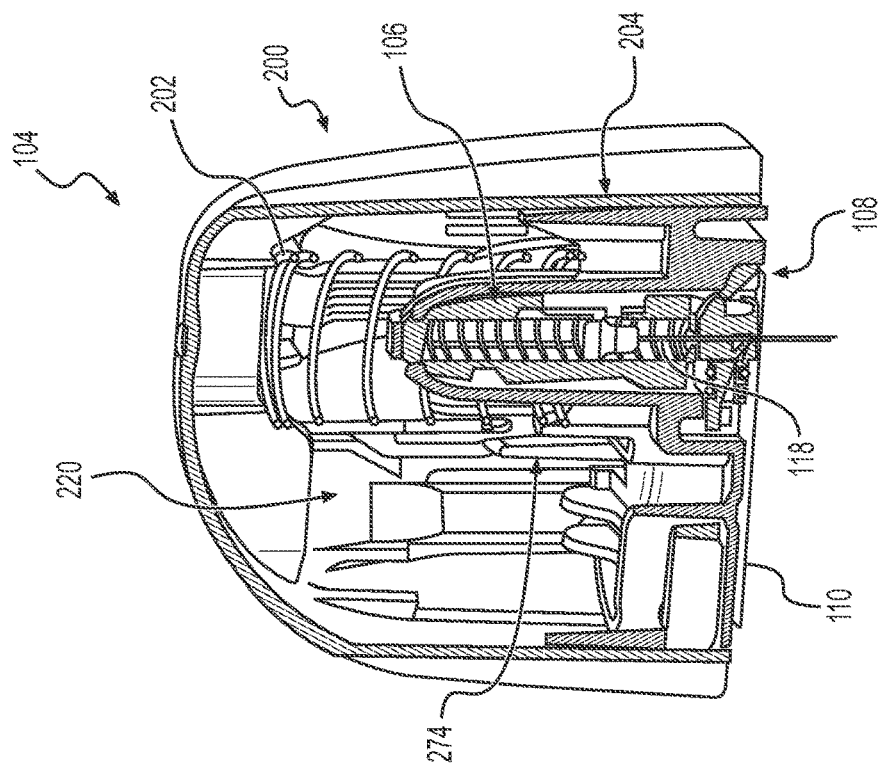
FIG. 8A is a cross-sectional view of the sensor inserter of FIG. 1, taken along line 8A-8A of FIG. 5C, which illustrates the physiological characteristic sensor assembly received within the sensor inserter in the first, shipping state.
Figure 8:
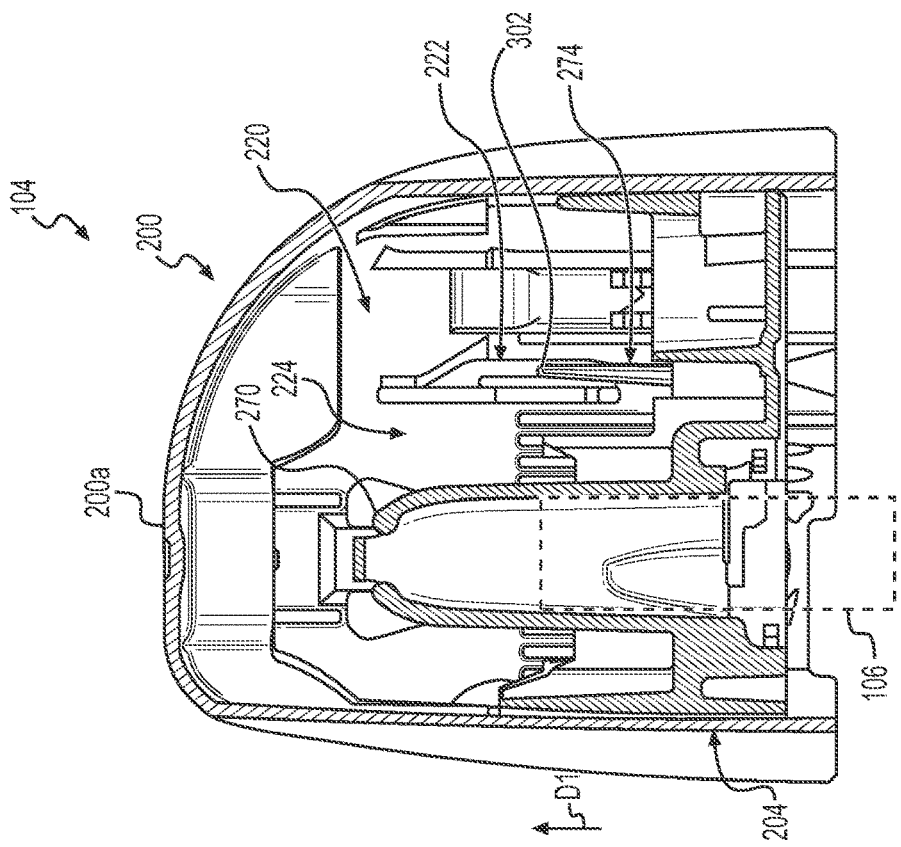
FIG. 8 is a cross-sectional view of the sensor inserter of FIG. 1, taken from the perspective of line 6-6 of FIG. 5, which illustrates the sensor inserter between the first, shipping state and a second, cocked state.
Figure 9:
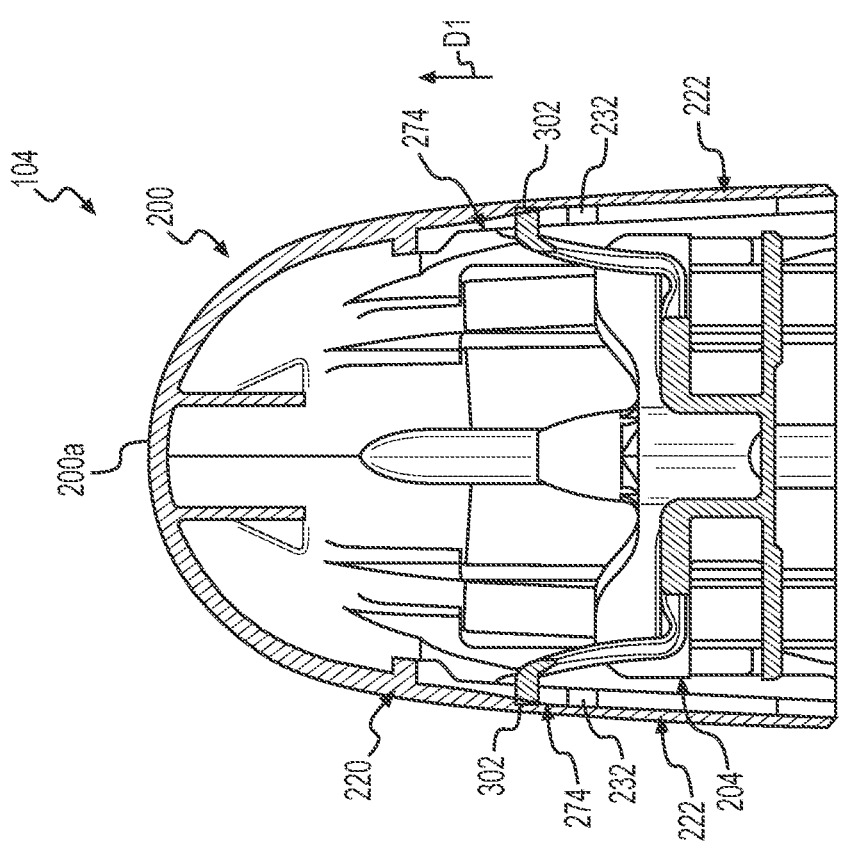
FIG. 9 is a cross-sectional view of the sensor inserter of FIG. 1, taken from the perspective of line 7-7 of FIG. 5, which illustrates the sensor inserter between the first, shipping state and the second, cocked state.

An exemplary deployment methodology for the glucose sensor 122 will now be described with reference to FIGS. 8-15. FIGS. 8 and 9 are each a cross-sectional views of the sensor inserter 104, with the spring 202 and the release body 206 removed for clarity. In one example, the sensor inserter 104 is placed over the physiological characteristic sensor assembly 102 and is pressed down to engage the sensor introducer 106 and to spring-load the insertion needle 118 as shown in FIG. 8A. In FIG. 8A, the packaging support 112 is removed for clarity. As the sensor introducer 106 is received within the sensor introducer receiving portion 270, with reference back to FIGS. 8 and 9, the striker 204 is moved relative to the housing 200, in a direction towards the top surface 200a. As the striker 204 moves upward, in the direction D1, the spring 202 (not shown) is compressed. In addition, as the striker 204 moves in the direction D1, the tabs 302 move upward within the first tracks 222. Generally, the sensor inserter 104 is pushed down over the physiological characteristic sensor assembly 102 until the sensor inserter 104 covers substantially all but feet 112a of the packaging support 112 (FIG. 1), which causes the movement of the striker 204 from the first, shipping state to the second, cocked state such that the sensor inserter 104 has moved from the first, shipping state to the second, cocked state.

Figure 11:
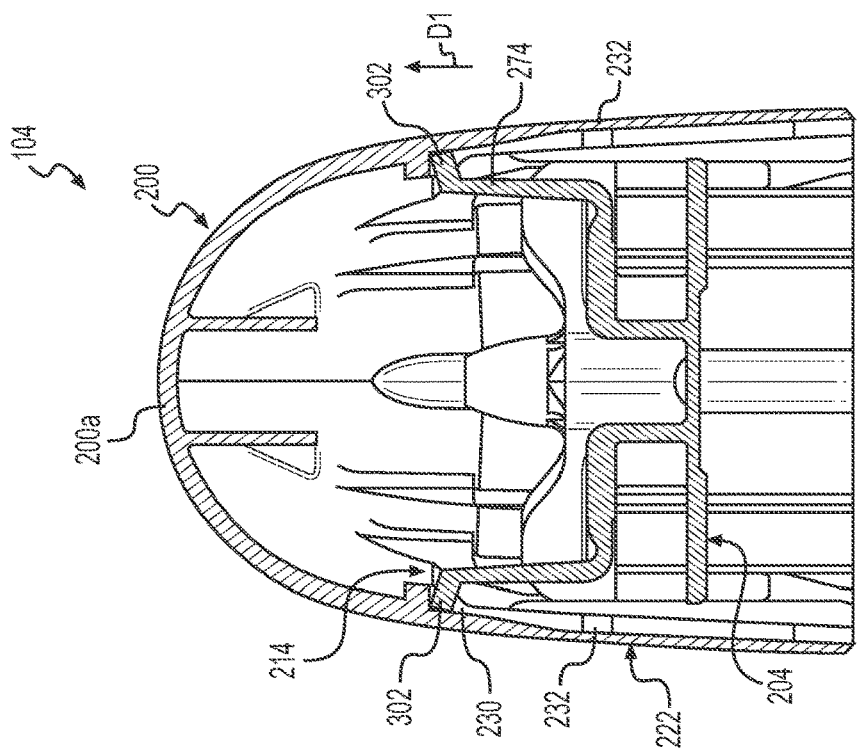
FIG. 11 is a cross-sectional view of the sensor inserter of FIG. 1, taken from the perspective of line 7-7 of FIG. 5, which illustrates the lock beam of the sensor inserter at the exit of the first track in accordance with various embodiments.
Figure 10:
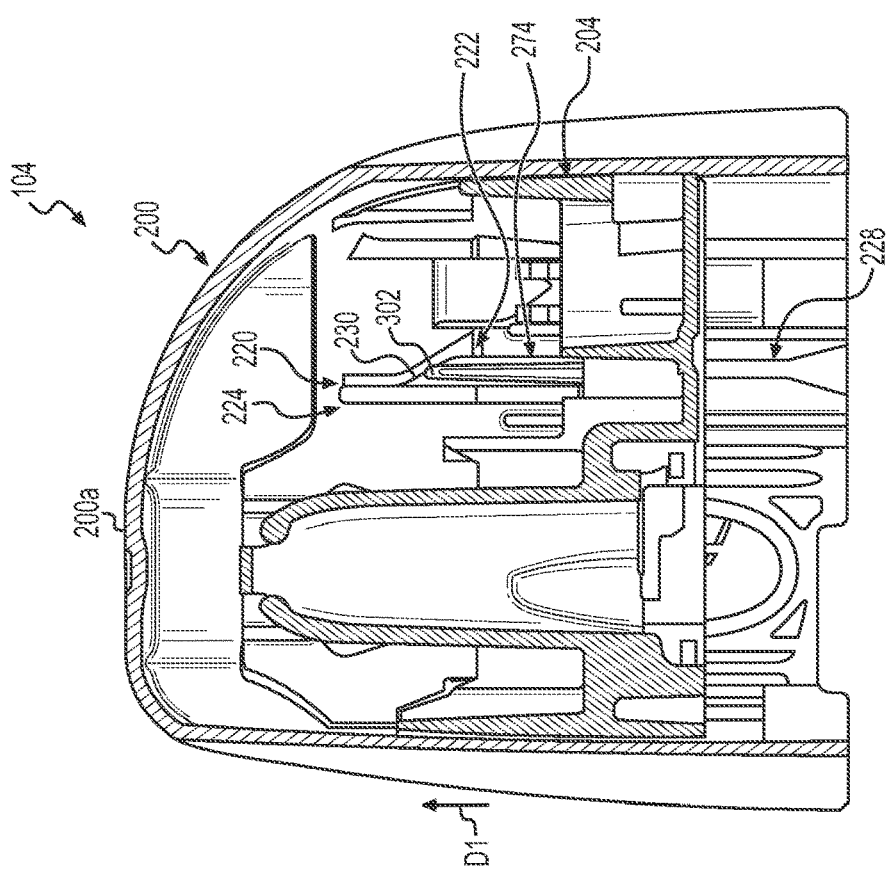
FIG. 10 is a cross-sectional view of the sensor inserter of FIG. 1, taken from the perspective of line 6-6 of FIG. 5, which illustrates a lock beam of the sensor inserter at an exit of a first track in accordance with various embodiments.

With reference to FIGS. 10 and 11, FIGS. 10 and 11 are each a cross-sectional views of the sensor inserter 104, with the spring 202 and the release body 206 removed for clarity. As shown, as the sensor introducer 106 is received further within the sensor introducer receiving portion 270, the striker 204 continues to move relative to the housing 200, in the direction D1 towards the top surface 200a. As the striker 204 moves upward, in the direction D1, the spring 202 (not shown) is further compressed. In addition, as the striker 204 moves in the direction D1, the tabs 302 move upward within the first tracks 222 to the exits 230.

Figure 12A:
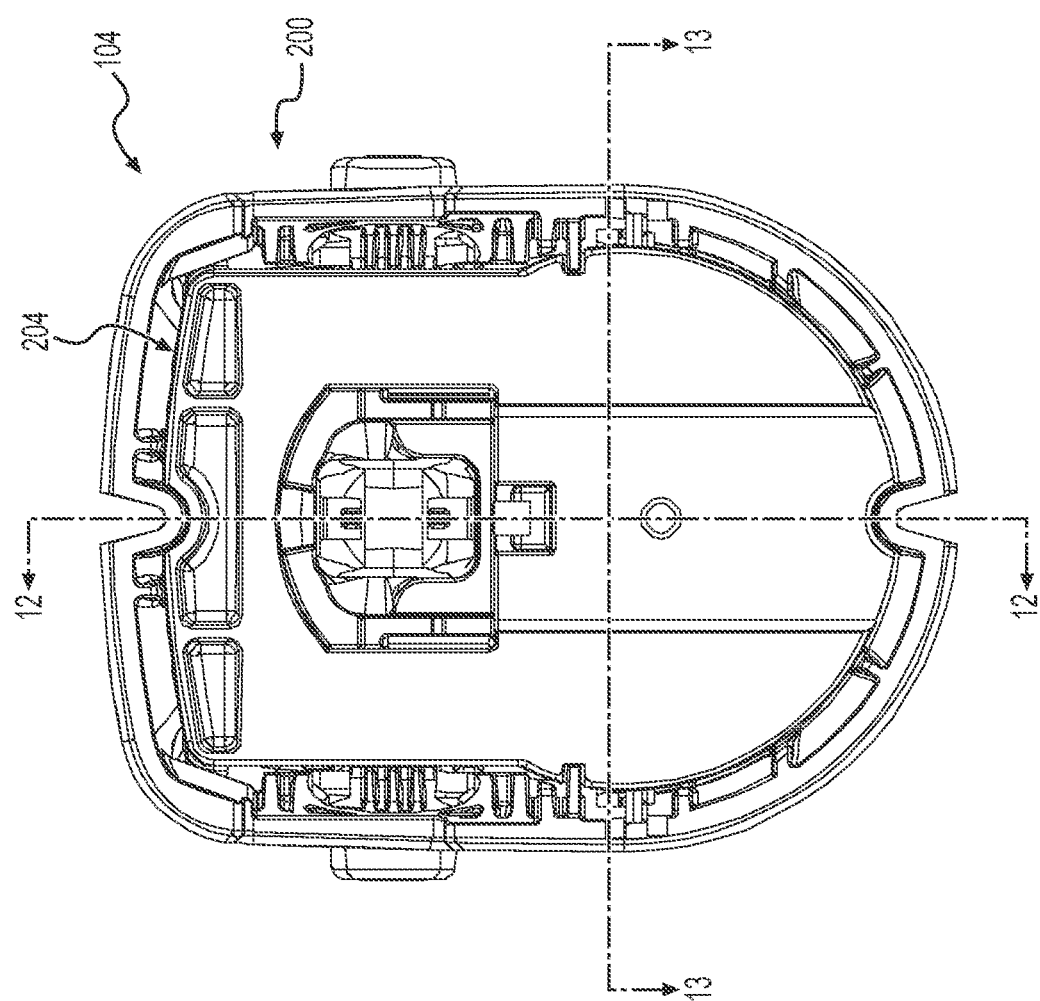
FIG. 12A is an end view of the sensor inserter of FIG. 1.
Figure 13:
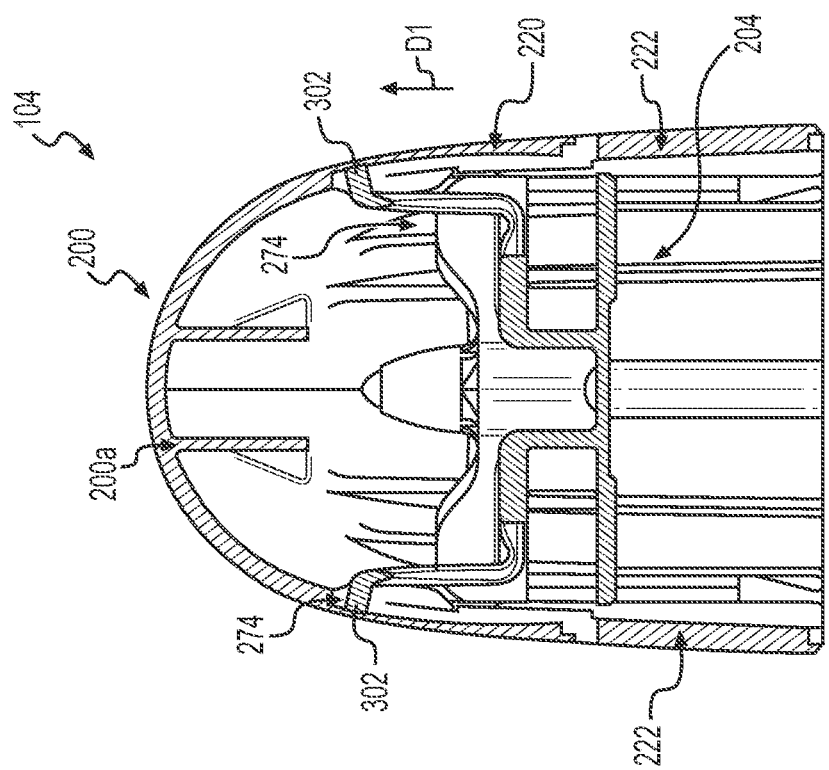
FIG. 13 is a cross-sectional view of the sensor inserter of FIG. 1, taken at line 13-13 of FIG. 12A, which illustrates the sensor inserter in the second, cocked state.
Figure 13A:
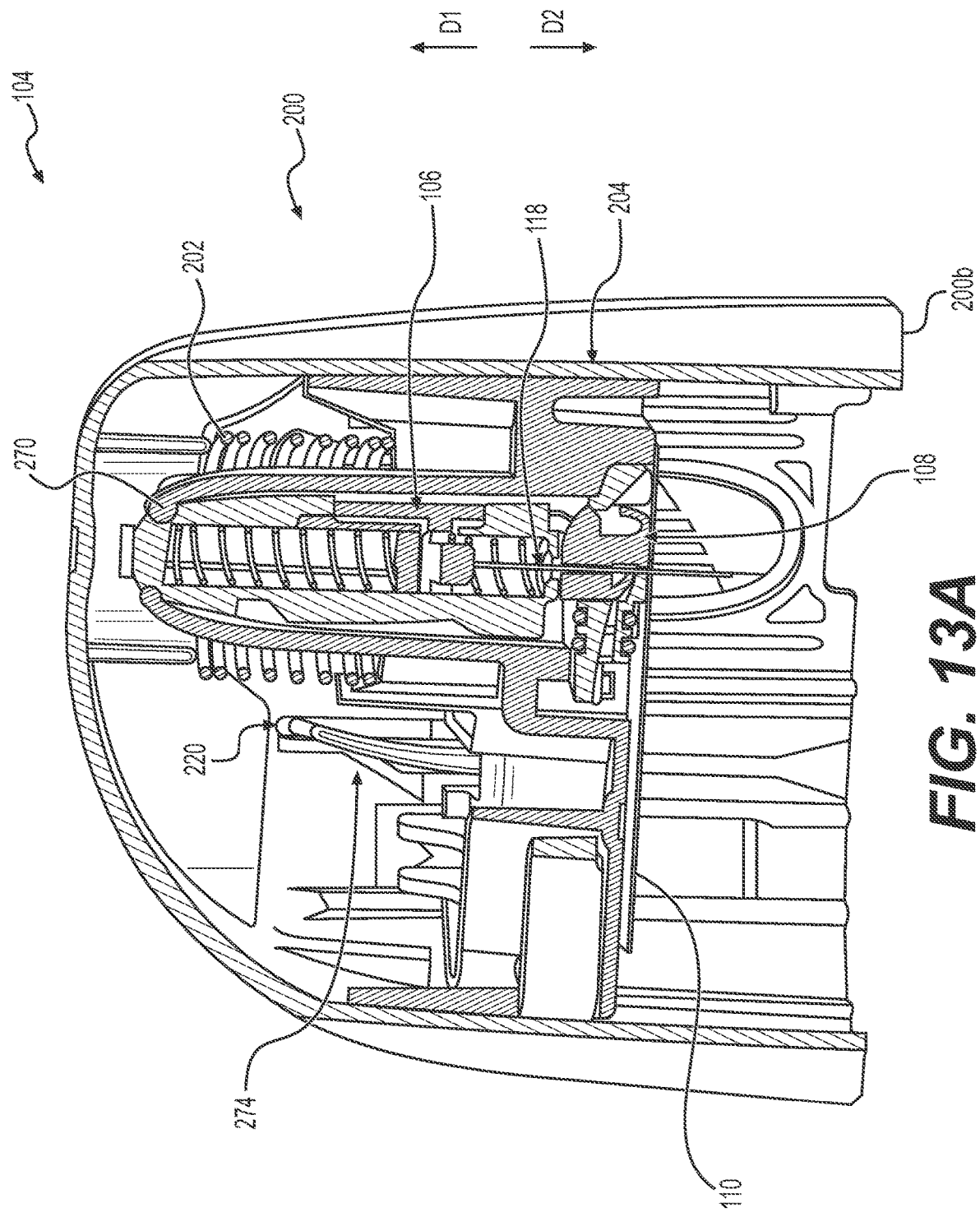
FIG. 13A is a cross-sectional view of the sensor inserter of FIG. 1, taken at line 13A-13A of FIG. 12A, which illustrates the sensor inserter in the second, cocked state.

With reference to FIGS. 12, 12A, 13 and 13A, FIGS. 12 and 13 are each a cross-sectional views of the sensor inserter 104 taken from FIG. 12A, with the spring 202 and the release body 206 removed for clarity. FIG. 13A is a cross-sectional view of the sensor inserter 104 taken from FIG. 12A, which includes the sensor introducer 106, the physiological characteristic sensor 108 and the adhesive patch 110. In FIGS. 12, 12A, 13 and 13A, the sensor inserter 104 is in the second, cocked state. FIG. 12A is a bottom view of the sensor inserter 104. As shown in FIGS. 12, 13 and 13A, as the sensor inserter 104 is pushed over the sensor introducer 106, the sensor introducer 106 contacts the sensor introducer receiving portion 270, and the continued advancement of the sensor inserter 104 in a direction D2 over the physiological characteristic assembly 102 causes the striker 204 to move relative to the housing 200, in the direction D1 towards the top surface 200a into the second, cocked state. As discussed, generally, the sensor inserter 104 is advanced over the sensor introducer 106 until all but the feet 112a of the packaging support 112 (FIG. 1) extend beyond the bottom surface 200b of the housing 200. As the striker 204 moves in the direction D1, the spring 202 (FIG. 13A) is further compressed. In addition, as the striker 204 moves in the direction D1 to the second, cocked state, the curved surface 234 (FIG. 12) of the first tracks 222 guide the tabs 302 from the first tracks 222 into the second tracks 224. The first steps 236 (FIG. 3) inhibit the tabs 302 from re-entering the first tracks 222. In the second, cocked state, the tabs 302 are engaged with the second tracks 224 in the distances 246 of the second tracks 224 that extend beyond the first tracks 222, as shown in FIG. 13A.

With the sensor inserter 104 in the second, cocked state, the sensor inserter 104 may be removed from the packaging support 112 (not shown). The packaging support 112 (not shown) is separated from the other components of the physiological characteristic sensor assembly 102 by lifting the sensor inserter 104 away from the packaging support 112 while holding onto the feet 112a of the packaging support 112 (FIG. 1). Removal of the packaging support 112 exposes the adhesive patch 110 and the remainder of the physiological characteristic sensor assembly 102 is retained within the interior of the sensor inserter 104, ready for deployment on the skin of the user. After removing the packaging support 112 from the assembly, the user moves the sensor inserter 104 to the desired deployment location, holds the sensor inserter 104 against the skin, and actuates the biasing tabs 212 of the housing 200 (see FIG. 4). Upon actuating of the biasing tabs 212, with reference to FIGS. 14 and 15, the striker 204 moves from the second, cocked state to the third, disposal state.

Figure 15:
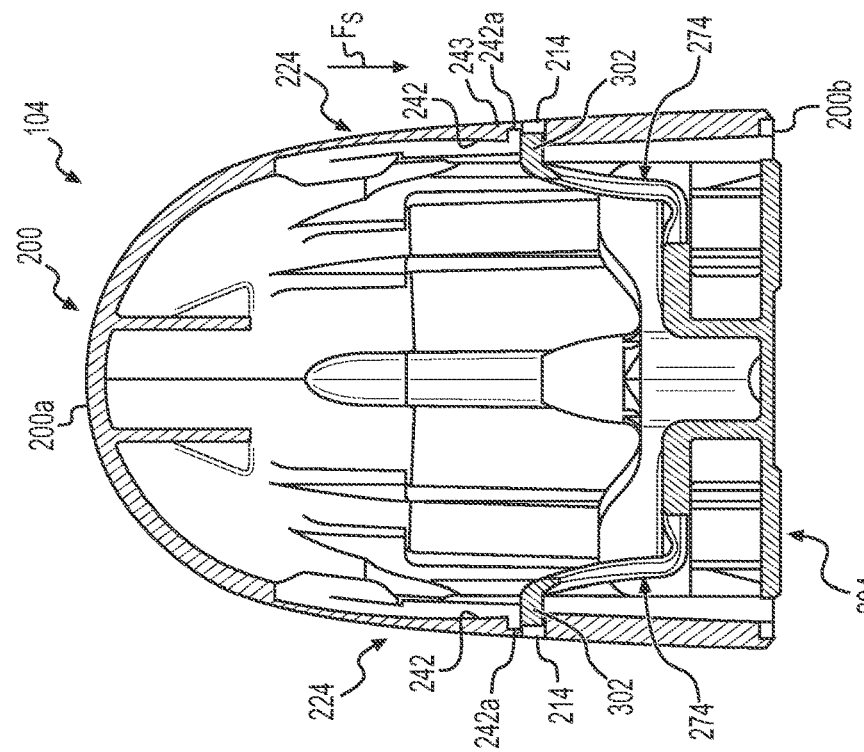
FIG. 15 is a cross-sectional view of the sensor inserter of FIG. 1, taken from the perspective of line 13-13 of FIG. 12A, which illustrates the sensor inserter in the third, disposal state.
Figure 14:
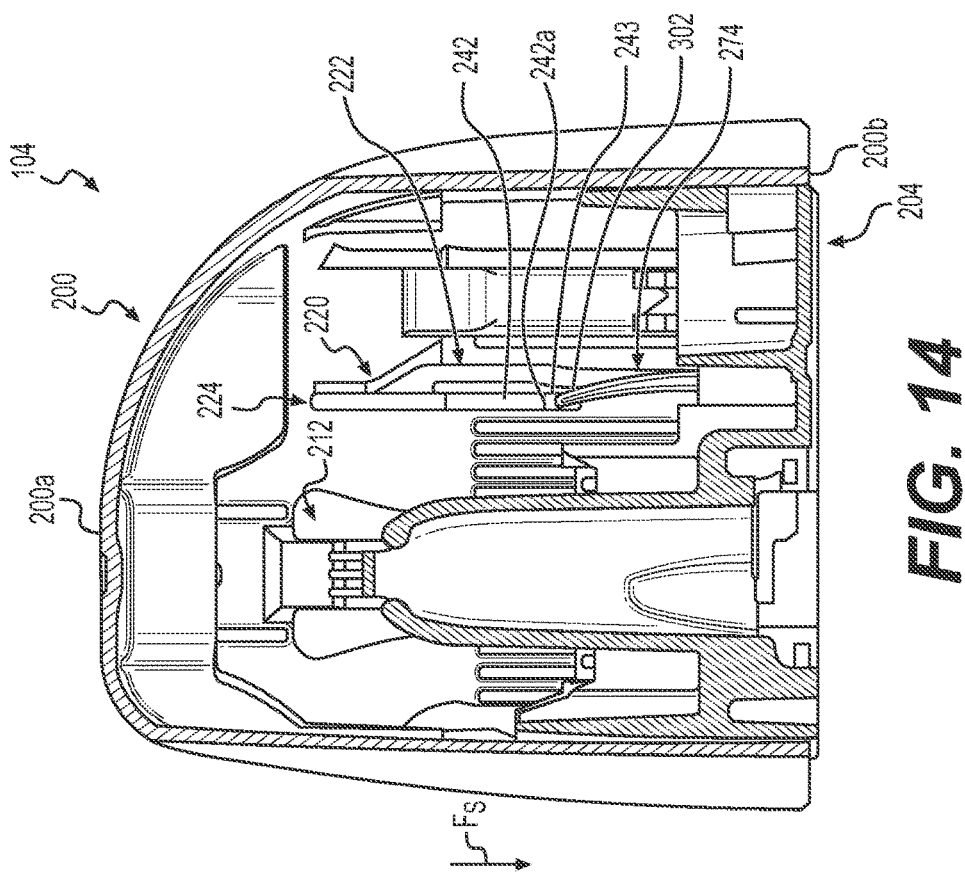
FIG. 14 is a cross-sectional view of the sensor inserter of FIG. 1, taken from the perspective of line 12-12 of FIG. 12A, which illustrates the sensor inserter in a third, disposal state.

FIGS. 14 and 15 are each a cross-sectional views of the sensor inserter 104, with the spring 202 and the release body 206 removed for clarity. In FIGS. 14 and 15, the sensor inserter 104 is in the third, disposal state. In the third, disposal state, the glucose sensor 122 (FIG. 1) is introduced into the anatomy and the adhesive patch 110 (FIG. 1) is coupled to the body of the user. In addition, in the third, disposal state, the sensor inserter 104 is inhibited from being reused to couple a replacement glucose sensor 122, for example, to the anatomy. As shown in FIGS. 14 and 15, actuation of the biasing tabs 212 compresses the biasing portion 312 of the release tabs 306 (FIG. 4), which moves the release tabs 306 from the stops 244 (FIG. 3). This enables the spring 202 to apply the spring force Fs to move the striker 204 from proximate the top surface 200a of the housing 200 to proximate the bottom surface 200b of the housing 200 to couple the glucose sensor 122 to the anatomy. As the striker 204 moves from the second, cocked state to the third, disposal state, the tabs 302 move along the second tracks 224 and over the ramps 242 into the second exits 243 and proximate the reset bores 214. The second steps 242a inhibit the tabs 302 from moving back up the second tracks 224. In the third, disposal state, the lock beams 274 are biased into the second exits 243. The movement of the striker 204 from the second, cocked state to the third, disposal state also moves the adhesive patch 110 into contact with the user's skin, and activates the insertion needle 118 to insert the glucose sensor 122 into the skin. Thereafter, the sensor inserter 104 is removed and separated from the sensor introducer 106 and the glucose sensor 122, which remains affixed to the skin by way of the adhesive patch 110. The sensor introducer 106 may then be removed from the glucose sensor 122.

In certain instances, the sensor inserter 104 may be moved from the first, shipping state to the second, cocked state and from the second, cocked state to the third, disposal state during manufacturing to ensure proper functioning of the sensor inserter 104. In these instances, with reference to FIG. 16, a special tool is inserted into the reset bores 214 to push the tabs 302 out of the second exit 243. As the lock beams 274 are biased in the second exit 243, the application of the force from the special tool causes the lock beams 274 to return to the unbiased position, which is the position the lock beams 274 are in when the sensor inserter 104 is in the first, shipping state. Thus, the reset bores 214 enable the sensor inserter 104 to be moved from the third, disposal state to the first, shipping state during manufacturing by moving the tabs 302 from the second track 224 to the first track 222.

Figure 17:
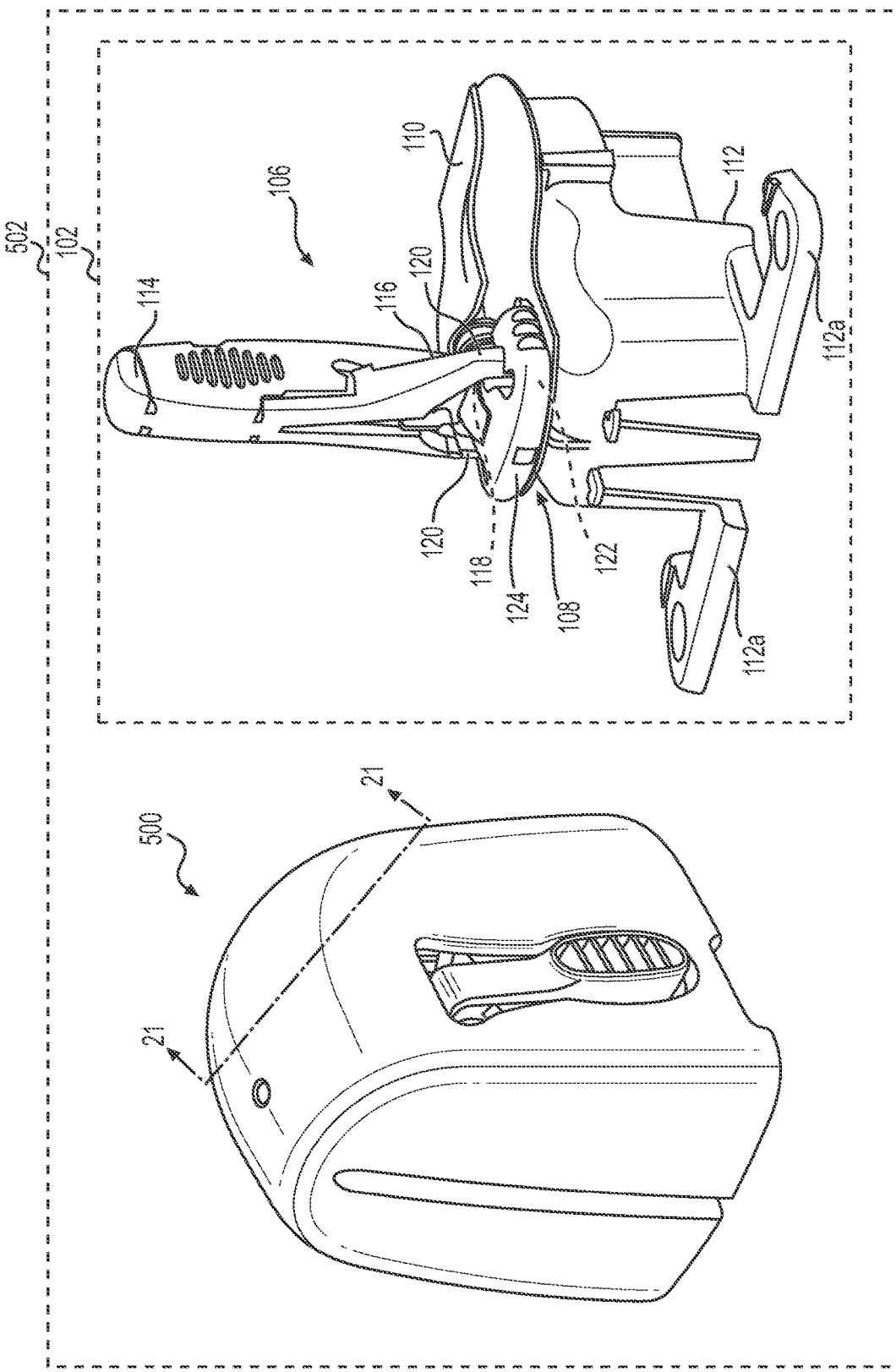
FIG. 17 is a schematic perspective view of an exemplary embodiment of a sensor introduction assembly that includes a sensor inserter with a disposal lockout state according to various teachings of the present disclosure.

It should be noted that in still other embodiments, the sensor inserter 104 may be configured differently to couple the glucose sensor 122 to a user while inhibiting a reuse of the sensor inserter 104. For example, with reference to FIG. 17, a sensor inserter 500 is shown. As the sensor inserter 500 includes the same or similar components as the sensor inserter 104 discussed with regard to FIGS. 1-16, the same reference numerals will be used to denote the same or similar components. FIG. 17 is a perspective view of a sensor introduction assembly 502. In one example, the sensor introduction assembly 502 includes the physiological characteristic sensor assembly 102 and the sensor inserter 500. The sensor inserter 500 is coupled to the sensor introducer 106 to remove the sensor introducer 106, the physiological characteristic sensor 108 and the adhesive patch 110 from the packaging support 112 to couple the glucose sensor 122 to the user. In one example, the sensor inserter 500 is sized to be positioned over at least the sensor introducer 106 and the physiological characteristic sensor 108.

Figure 18:
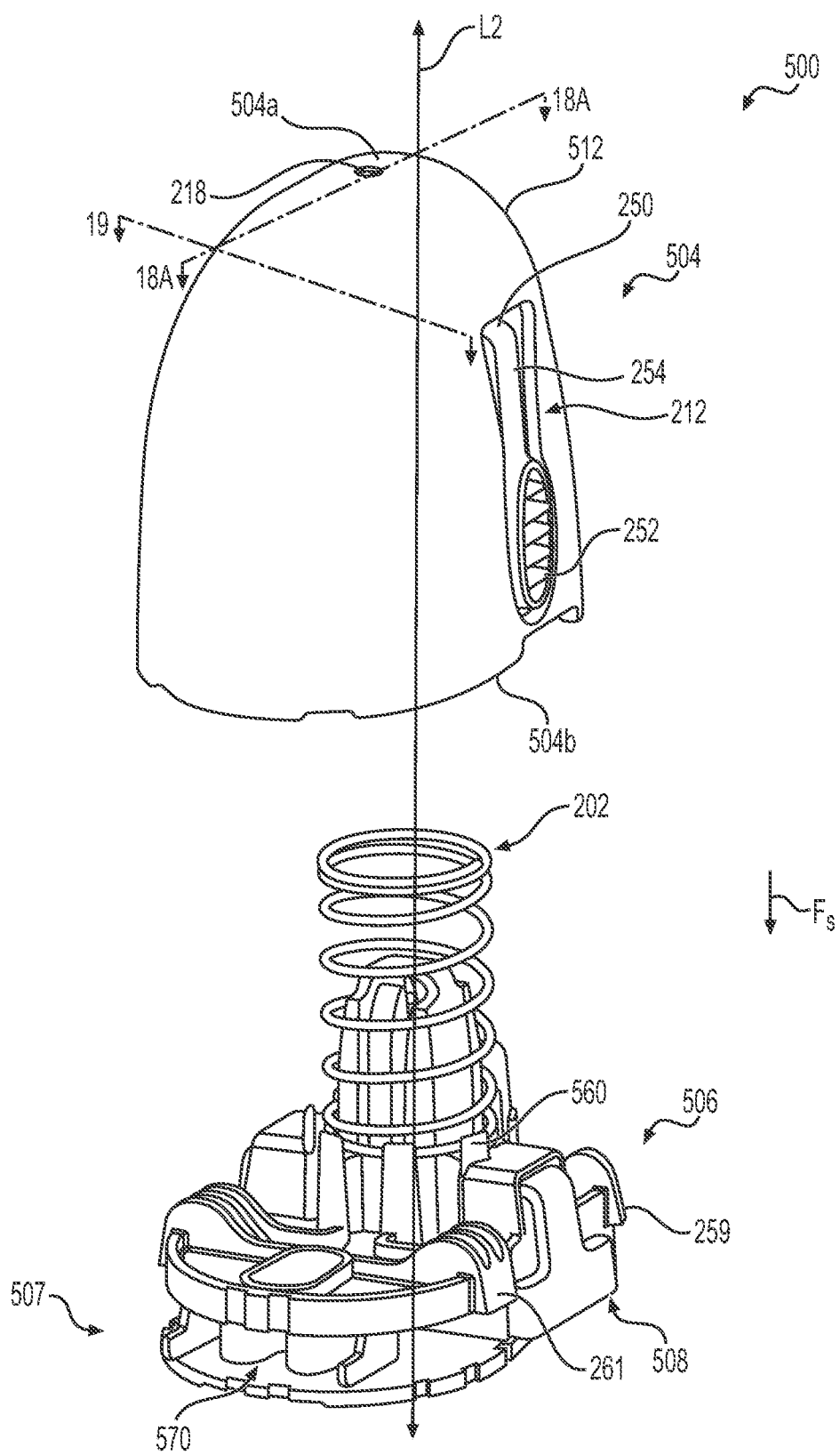
FIG. 18 is a partially exploded view of the sensor inserter of FIG. 17.

With reference to FIG. 18, a partially exploded view of the sensor inserter 500 is shown. The sensor inserter 500 includes a housing 504, the biasing member or spring 202, a striker 506, a pair of release tabs 508 and a lock beam 510. The striker 506, the pair of release tabs 508 and the lock beam 510 form a striker assembly 507. The housing 504 is substantially U-shaped, and receives the spring 202, the striker 506, the pair of release tabs 508 and the lock beam 510. The housing 504 is generally symmetric with respect to a longitudinal axis L2, which extends through the housing 504. The housing 504 is composed of a polymer-based material, including, but not limited to acrylonitrile butadiene styrene, polyoxymethylene, polyamide, polyethylene, polypropylene, polyvinyl chloride, polycarbonate, or the like. The housing 504 may be formed by injection molding, casting, etc. The housing 504 includes an outer surface 512 opposite an inner surface 514 (FIG. 19), the pair of biasing tabs 212 and the spring guide 217 (FIG. 19). The housing 504 also includes a first, top surface 504a opposite a second, bottom surface 504b. The bottom surface 504b is circumferentially open to enable the spring 202, the striker 506, the pair of release tabs 508 and the lock beam 510 to be received within the housing 504, and for the housing 504 to be positioned over at least the sensor introducer 106 and the physiological characteristic sensor 108. Thus, the bottom surface 504b defines a bore, through which the spring 202, the striker 506, the pair of release tabs 508 and the lock beam 510 are received within the housing 504, and that enables the housing 504 to be positioned over at least the sensor introducer 106 and the physiological characteristic sensor 108. The outer surface 512 may include the depression 218. The housing 504 may also include one notch 216 that cooperates with the striker 506 to guide the movement of the striker 506 within and relative to the housing 504.

With reference to FIG. 19, a cross-section of the housing 504 is shown. As shown in FIG. 19, the inner surface 514 defines at least one track system 520. In this example, the inner surface 514 defines two track systems 520, one on each side of the housing 504. The track systems 520 cooperate with a portion of the lock beam 510 to move the sensor inserter 500 between a first, shipping state to a second, cocked state and from the second, cocked state to a third, disposal state. As the track systems 520 are the same and symmetric with respect to the longitudinal axis L2, a single one of the track systems 520 will be described herein. In this example, the track system 520 is defined on the inner surface 514 so as to be spaced apart from one of the pair of biasing tabs 212. Generally, the track system 520 is defined as a recess on the inner surface 514 that does not extend to the outer surface 512 (FIG. 18). In one example, the track system 520 includes a first track 522 and a second track 524.

The first track 522 extends from the bottom surface 504b of the housing 504 toward the top surface 504a. The first track 522 guides the portion of the lock beam 510 as the sensor inserter 500 moves from the first, shipping state to the second, cocked state. With reference to FIG. 19A, the first track 522 includes an entrance 526, an intermediate track portion 528 and an exit 530. The entrance 526 is defined at the bottom surface 504b, and may include a curved surface 526a to assist in guiding the portion of the lock beam 510 into the first track 522. The intermediate track portion 528 extends from the entrance 526 to the exit 530. The intermediate track portion 528 includes a sloped surface 532, which guides the portion of the lock beam 510 in a direction F2, which is transverse to the longitudinal axis L2. The exit 530 is in communication with the second track 524. The exit 530 has a second curved surface 534, which assists in directing the portion of the lock beam 510 into the second track 524. The second curved surface 534 extends a distance outward from the inner surface 514 to ensure that the portion of the lock beam 510 remains within the first track 522 and transitions into the second track 524 at the exit 530.

Generally, the first track 522 is defined at a first depth DT5, which is different than a second depth DT6 of the second track 524. In one example, the first depth DT5 is less than the second depth DT6, such that once the portion of the lock beam 510 has entered the second track 524, a first step 536 is defined between the first depth DT5 and the second depth DT6 that retains the portion of the lock beam 510 within the second track 524. In one example, the first step 536 has a thickness ST2 of about 0.5 millimeters (mm) to about 1.5 millimeters (mm). The first track 522 generally extends along a first axis A5 and the second track 524 extends along a second axis A6. The first axis A5 and the second axis A6 are substantially parallel, and are substantially parallel to the longitudinal axis L2 (FIG. 19).

The second track 524 extends from near the top surface 504a to the bottom surface 504b. The second track 524 guides the portion of the lock beam 510 as the sensor inserter 500 moves from the second, cocked state to the third, disposal state. The second track 524 includes a second entrance 540, an intermediate track portion 541, a ramp 542 and a second exit 543. The second entrance 540 is in communication with the exit 530 of the first track 522. The second entrance 540 extends for a distance 546 along the longitudinal axis L2 that is beyond the exit 530 to enable a movement of the striker 506 to the second, cocked state prior to entering the third, disposal state. The intermediate track portion 541 interconnects the second entrance 540 and the ramp 542. The intermediate track portion 541 includes a slanted surface 541a, which assists in directing the portion of the lock beam 510 to the ramp 542.

The ramp 542 guides the portion of the lock beam 510 from the second, cocked state to the third, disposal state. The ramp 542 is positioned between the intermediate track portion 541 and the second exit 543. The ramp 542 is inclined relative to the second entrance 540 and a surface of the second track 524 with a positive slope, which causes a compression of the portion of the lock beam 510 such that once the portion of the lock beam 510 moves beyond the ramp 542, the portion of the lock beam 510 expands into the second exit 543. The incline of the ramp 542 also inhibits the portion of the lock beam 510 from moving back over the ramp 542 by defining a second step 542a. The second step 542a is generally planar, and inhibits the retraction or rearward movement of the portion of the lock beam 510 once the portion of the lock beam 510 has moved over the ramp 542. Thus, the second step 542a cooperates with the lock beam 510 to inhibit reusing of the sensor inserter 500. Generally, a wall 549 that separates the first track 522 from the second track 524 extends for a distance from the inner surface 514 to ensure that the portion of the lock beam 510 remains within the second track 524 as the portion of the lock beam 510 moves down the ramp 542. The second exit 543 is proximate the bottom surface 504b. The sensor inserter 500 is in the third, disposal state when the portion of the lock beam 510 is received within the second exit 543 and is proximate the bottom surface 504b.

In one example, a passage 548 is defined beneath the exit 530 and the second exit 543 along the bottom surface 504b. The passage 548 enables the insertion of a special tool to reset the sensor inserter 500 from the third, disposal state to the first, shipping state, as will be discussed further herein. Generally, the passage 548 is defined to extend along the bottom surface 504b from an area proximate the exit 530 to an area beyond, but proximate to, the second exit 543.

Figure 18A:
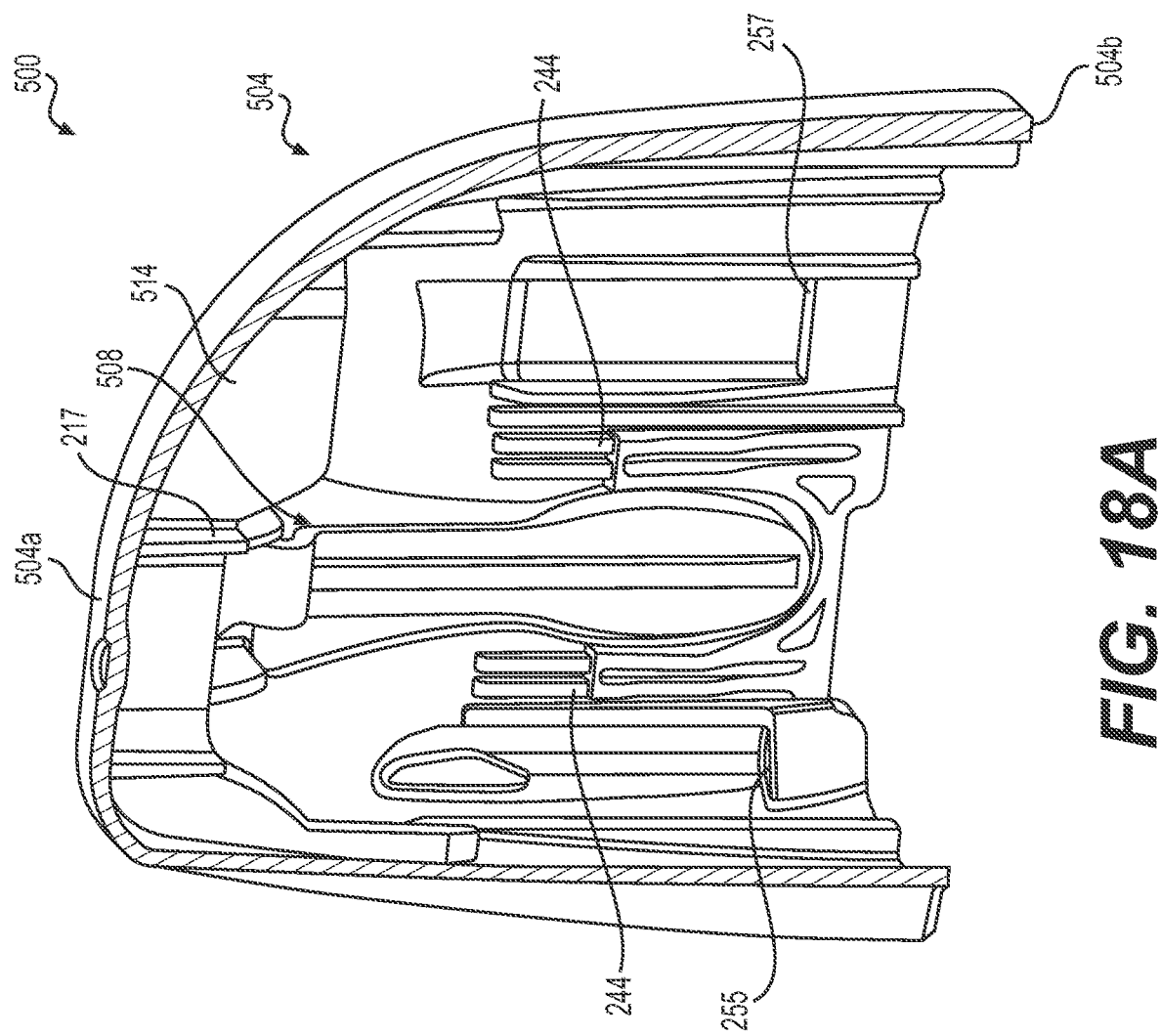
FIG. 18A is a cross-sectional view of a housing of the sensor inserter of FIG. 17, taken along line 18A-18A of FIG. 18.

With reference to FIG. 18A, the inner surface 514 also defines the pair of stops 244 for the pair of release tabs 508 (FIG. 18). The stops 244 are defined on opposed sides of the housing 504, and in one example, are each defined proximate a respective one of the pair of biasing tabs 212. The stops 244 receive and support a respective one of the pair of release tabs 508 in the second, cocked state, and the striker 506 may be released from the stops 244 by the user manipulating the biasing tabs 212. The housing 504 may also include the first retention catches 255 and the second retention catches 257, which cooperate with the first retention snaps 259 and the second retention snaps 261 (FIG. 18) enable the assembly of the striker 506 to the housing 504.

With reference back to FIG. 18, the pair of biasing tabs 212 are identical and symmetric with respect to the longitudinal axis L2. The housing 504 may include a pair of cut-out regions 504c, which enables the movement of the biasing tabs 212 relative to the housing 504. The graspable portion 252 provides a surface for the user to manipulate to move the biasing tab 212 relative to the housing 504. In one example, the graspable portion 252 is pushed inward by the user to release the striker 506 for coupling the glucose sensor 122 to the anatomy. With reference to FIG. 18A, the spring guide 217 is defined to extend inwardly from the top surface 504a toward the bottom surface 504b. The spring guide 217 acts as a spring seat, and maintains a position of the spring 202 within the housing 504. With reference to FIG. 18, the spring 202 biases the striker 506 from the second, cocked state to the third, disposal state. The spring 202 applies the spring force Fs to the striker 506 to move the striker 506 from near the top surface 504a of the housing 504 (in the second, cocked state) to the third, disposal state. An end of the spring 202 is positioned about the spring guide 217 and an opposing end of the spring 202 is positioned about a spring seat 560 of the striker 204.

Figure 20:
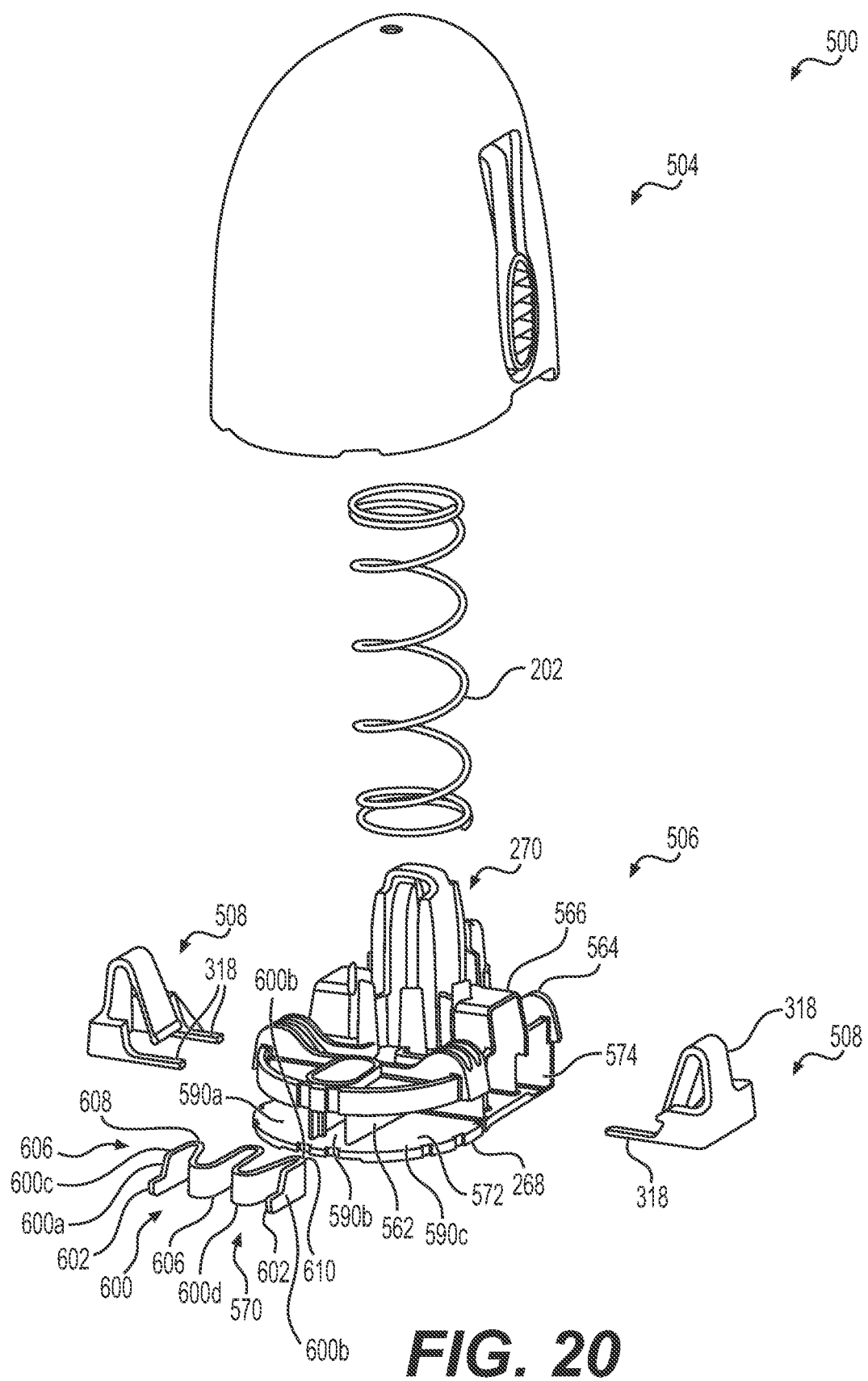
FIG. 20 is an exploded view of the sensor inserter of FIG. 17.

With reference to FIG. 18, the striker 506 is movable relative to the housing 504 to couple the glucose sensor 122 (FIG. 1) to the user. In one example, with reference to FIG. 20, the striker 506 includes a first end 562 opposite a second end 564, a top striker surface 566 opposite the bottom striker surface 268, the sensor introducer receiving portion 270, a beam receiving channel 572 and a pair of pockets 574. The striker 506 is composed of a polymer-based material, including, but not limited to acrylonitrile butadiene styrene, polyoxymethylene, polyamide, polyethylene, polypropylene, polyvinyl chloride, polycarbonate, or the like. The striker 506 may be formed by injection molding, casting, etc. The striker 506 is symmetric with respect to the longitudinal axis L2.

Figure 23:
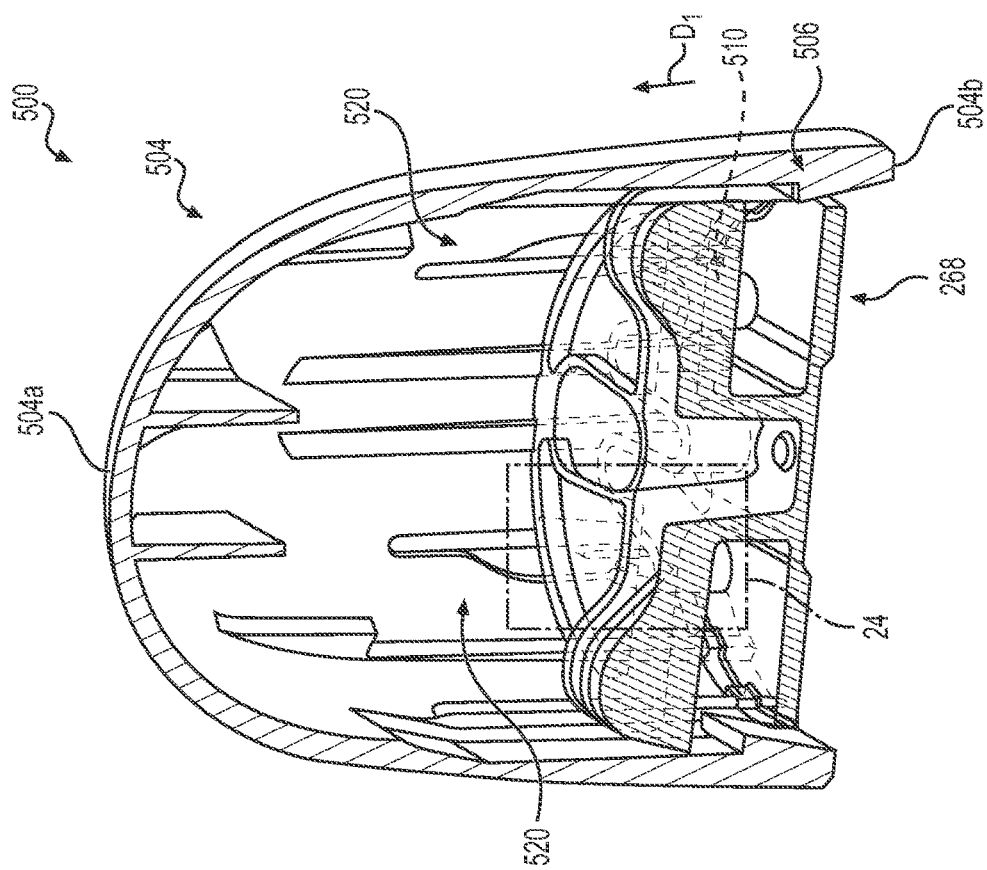
FIG. 23 is a cross-sectional view of the sensor inserter of FIG. 17, taken from the perspective of line 21-21 of FIG. 17, which illustrates the sensor inserter between the first, shipping state and a second, cocked state.
Figure 23C:
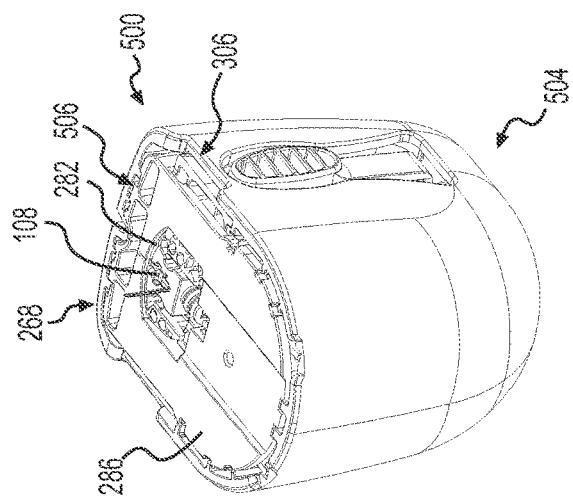
FIG. 23C is an end view of the sensor inserter of FIG. 17, in which the physiological characteristic sensor assembly is coupled to the sensor inserter and an adhesive patch is removed from the physiological characteristic sensor assembly for clarity.
Figure 23A:
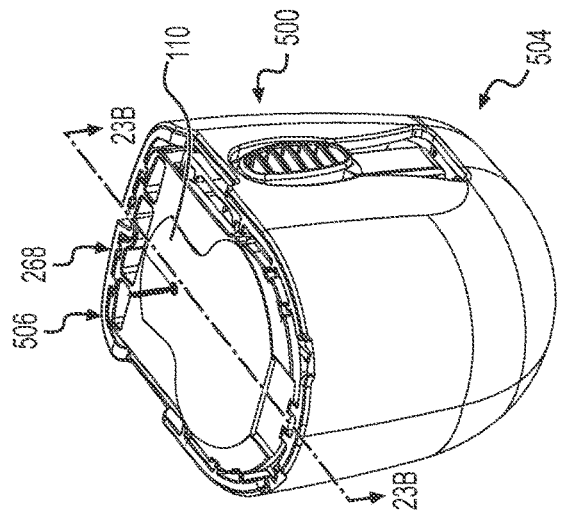
FIG. 23A is an end view of the sensor inserter of FIG. 17, in which a physiological characteristic sensor assembly is coupled to the sensor inserter.
Figure 23B:
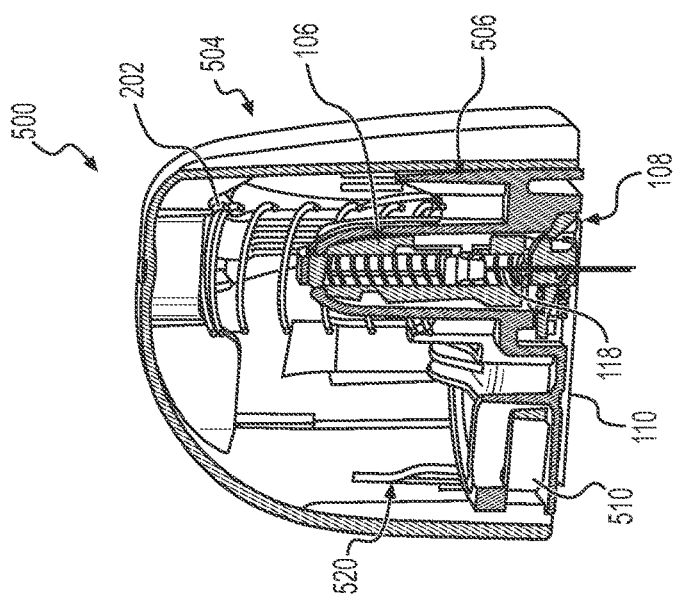
FIG. 23B is a cross-sectional view of the sensor inserter of FIG. 17, taken along line 23B-23B of FIG. 23A, which illustrates the physiological characteristic sensor assembly received within the sensor inserter in the first, shipping state.
Figure 31:
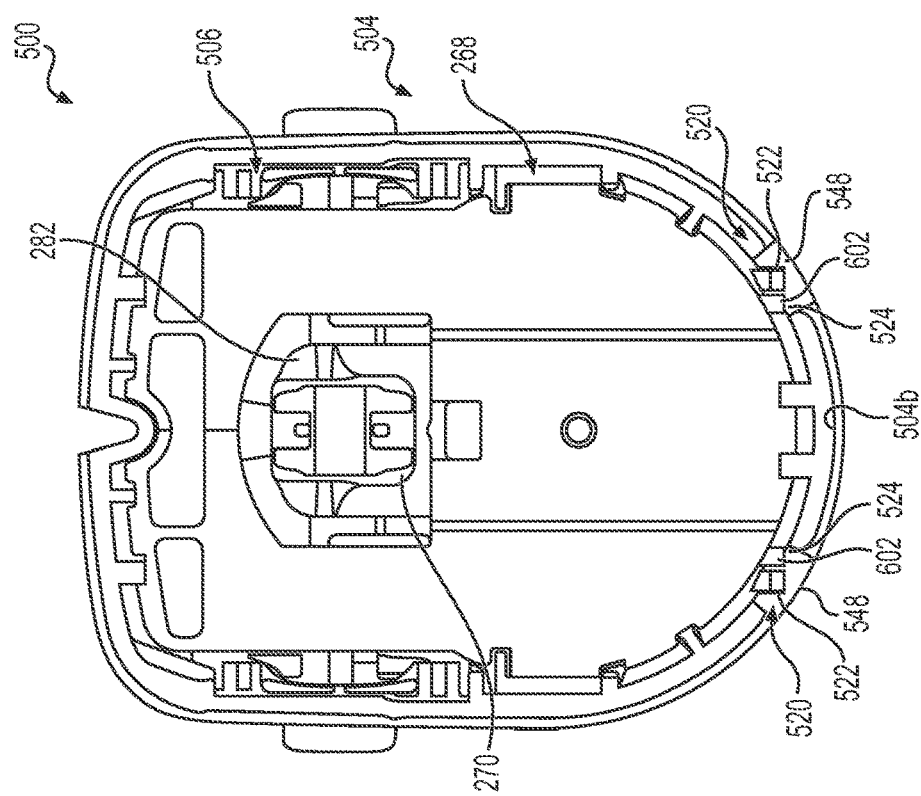
FIG. 31 is an end view of the sensor inserter of FIG. 17, which illustrates the sensor inserter in the third, disposal state.

The top striker surface 566 defines the spring seat 560. In one example, the spring seat 560 is defined about a perimeter of the sensor introducer receiving portion 270, which extends axially from the top striker surface 566. The bottom striker surface 268 receives the sensor introducer 106, the physiological characteristic sensor 108 and the adhesive patch 110 (FIG. 23A-23C) to couple the sensor introducer 106, the physiological characteristic sensor 108 and the adhesive patch 110 to the sensor inserter 500. In FIG. 23A-23C, the packaging support 112 is removed for clarity, and in FIG. 23C, the adhesive patch 110 is removed for clarity. The sensor introducer receiving portion 270 extends from the top striker surface 266 and is in communication with the bore 282 (FIG. 31). The sensor introducer receiving portion 270 cooperates with the sensor introducer 106 such that as the sensor introducer 106 is received within the sensor introducer receiving portion 270, the sensor introducer 106 moves the striker 506 relative to the housing 504.

The beam receiving channel 572 receives the lock beam 510 and is defined proximate the first end 562. The beam receiving channel 572 generally defines a plurality of slots 590a-590c that each receive a corresponding portion of the lock beam 510. The pair of pockets 574 each receive a respective one of the release tabs 508 and are defined proximate the second end 564. Each of the pockets 574 is defined to enable the respective one of the release tabs 508 to move relative to the striker 506 to enable the striker 506 to move from the second, cocked state to the third, disposal state.

The pair of release tabs 508 include the contact portion 310 and the biasing portion 312. Generally, the release tabs 508 are movable relative to the striker 506 and the housing 504 between the expanded state and the compressed state. The pair of release tabs 508 are each composed of a polymer-based material, including, but not limited to acrylonitrile butadiene styrene, polyoxymethylene, polyamide, polyethylene, polypropylene, polyvinyl chloride, polycarbonate, or the like. The pair of release tabs 508 may be formed by injection molding, casting, etc. The contact portion 310 is sized to be contacted by a respective one of the biasing tabs 212 when the user manipulates the biasing tabs 212 into the housing 504. The contact portion 310 also contacts the stops 244 of the housing 504 to retain the striker 506 in the second, cocked state. The biasing portion 312 is received into a respective one of the pockets 574 of the striker 506, and is movable to engage or disengage the contact portion 310 with the stops 244 of the housing 504. The biasing portion 312 is compressible into the compressed state by the application of a force by the user's manipulation of the biasing tabs 212 to disengage the contact portion 310 with the stops 244 to move the striker 506 to the third, disposal state. Each of the release tabs 508 include the pair of projecting legs 318 to inhibit twisting of the release tab 508, for example, as the release tab 508 is compressed into the compressed state.

The lock beam 510 cooperates with the track systems 520 to inhibit the reuse of the sensor inserter 500. The lock beam 510 is composed of a polymer-based material, a metal or a metal alloy, including, but not limited to acrylonitrile butadiene styrene, polyoxymethylene, polyamide, polyethylene, polypropylene, polyvinyl chloride, polycarbonate, stainless steel, beryllium copper, shape memory alloy, or the like. The lock beam 510 may be formed by injection molding, casting, etc. The lock beam 510 includes a body 600 and a pair of tabs 602. The body 600 includes a plurality of undulations 604, which impart flexibility to the lock beam 510. In addition, the plurality of undulations 604 cooperate with the slots 590a-590c to retain the lock beam 510 within the striker 506. In one example, a first peak 606 of the plurality of undulations 604 is received within the slot 590b to retain the lock beam 510 within the striker 506. Second peak 608 and third peak 610 are received within slots 590a, 590c, respectively, and are movable within the slots 590a, 590c to enable the tabs 602 to engage with the first track 522 and the second track 524 (FIG. 19A). The tabs 602 are rectangular, and each extends from an opposing end 600a, 600b of the body 600 to engage with the track systems 520. The tabs 602 generally extend at the opposing ends 600a, 600b from a second, bottom surface 600d of the lock beam 510 toward an opposed first, top surface 600c of the lock beam 510. By providing the body 600 with the undulations 604, as the tabs 602 move within the track systems 520, the body 600 enables the lock beam 510 to be relaxed or uncompressed when the tabs 602 are engaged with the first track 522, and biased or compressed when the tabs 602 are engaged with the second tracks 524 (FIG. 19). Thus, the lock beam 510 is movable relative to the striker 506 as the lock beam 510 transitions from the first track 522 to the second track 524.

In one example, in order to assemble the sensor inserter 500, with the housing 504, the striker 506, the pair of release tabs 508 and the lock beam 510 formed, the pair of release tabs 508 are coupled to the pockets 574 of the striker 506. In one example, the each of the release tabs 508 are coupled to the respective pocket 574 with a snap-fit. The lock beam 510 is coupled to the striker 506, such that the first peak 606 is received within the slot 590b. In one example, the lock beam 510 is coupled to the striker 506 with a snap-fit. The spring 202 is coupled to the striker 506 so as to be positioned about the sensor introducer receiving portion 270. The housing 504 is coupled to the striker 506. In one example, the housing 504 is coupled to the striker 506 with a snap-fit.

Figure 22:
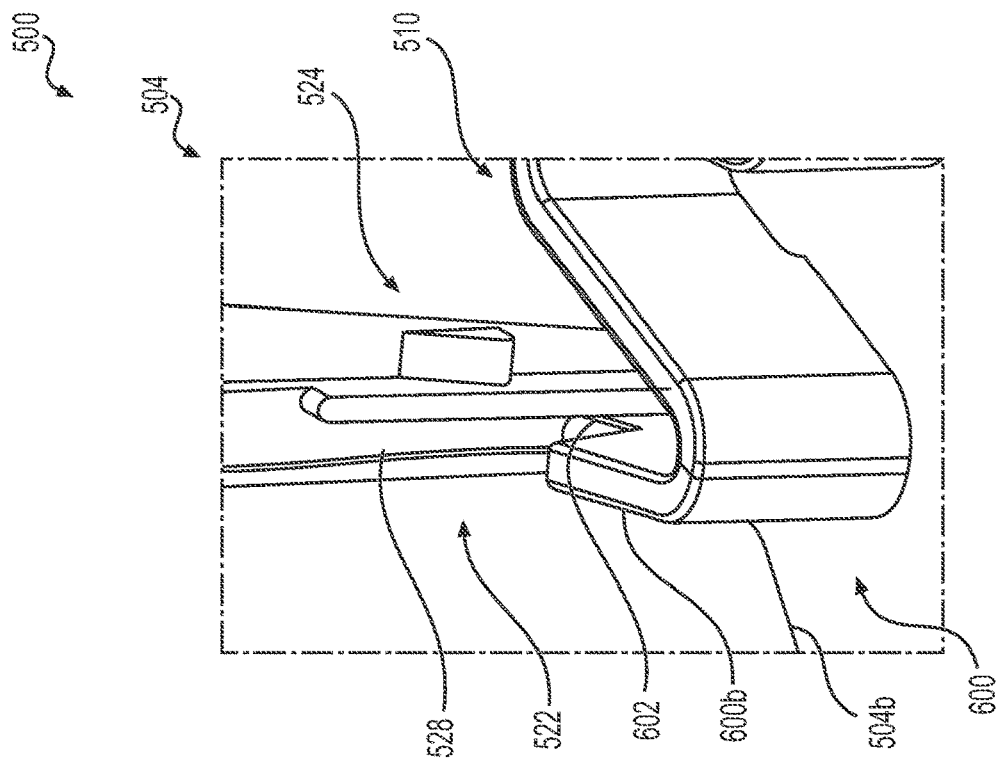
FIG. 22 is a detail view of the sensor inserter of FIG. 21, taken at 22 of FIG. 21.
Figure 21:
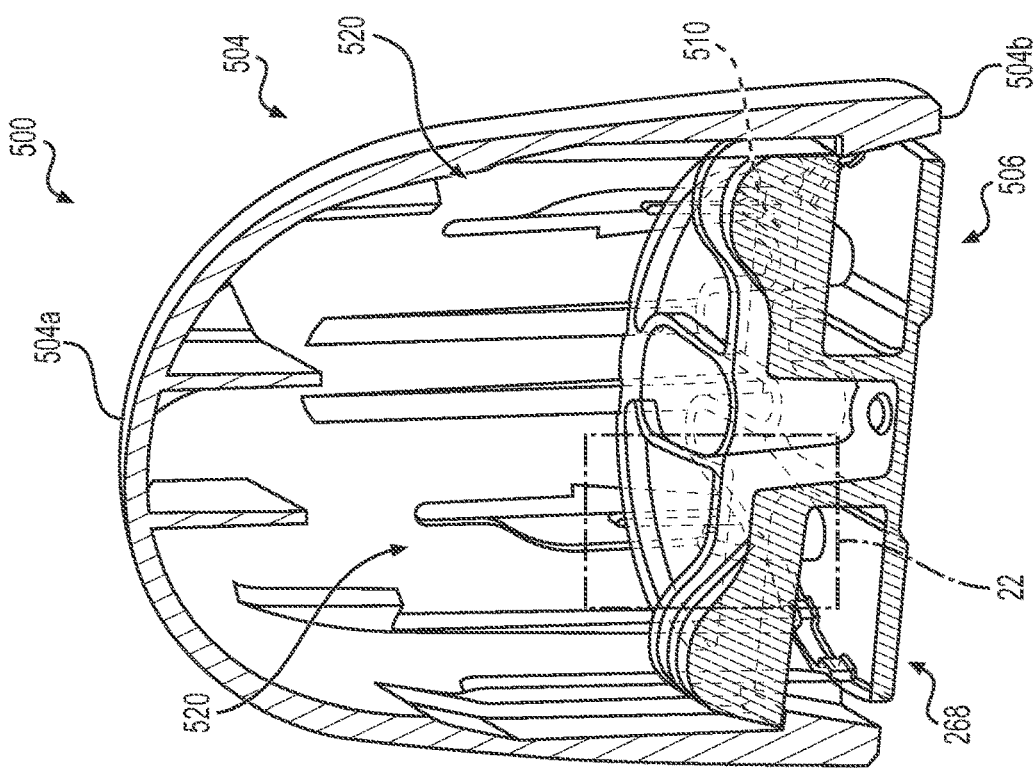
FIG. 21 is a cross-sectional view of the sensor inserter of FIG. 17, taken along line 21-21 of FIG. 17, which illustrates the sensor inserter in a first, shipping state.

With the sensor inserter 500 assembled, the sensor inserter 500 may be used to couple the glucose sensor 122 (FIG. 17) to an anatomy of a user. In one example, with reference to FIGS. 21 and 22, the sensor inserter 500 is in the first, shipping state. FIGS. 21 and 22 are each a cross-sectional views of the sensor inserter 500, in which the spring 202 and the pair of release tabs 508 have been removed for clarity. In the first, shipping state, the sensor introducer receiving portion 270 (not shown) is spaced apart from the top surface 504a of the housing 504, and the bottom striker surface 268 extends slightly beyond the bottom surface 504b of the housing 504. In the first, shipping state, the tabs 602 are each engaged with the intermediate track portion 528 of the first track 522, as shown for one of the tabs 602 in FIG. 22. In the first, shipping state, the sensor inserter 500 may be packaged, in suitable packaging, for receipt by the consumer or user.

With brief reference to FIG. 17, with the sensor introducer 106, the glucose sensor 122, the sensor base 124, the adhesive patch 110 and the packaging support 112 formed, the physiological characteristic sensor assembly 102 may be assembled. In one example, the glucose sensor 122 is coupled to the sensor base 124, and this assembly is coupled to the adhesive patch 110. The adhesive patch 110 is coupled to the packaging support 112. The sensor introducer 106 is coupled to the sensor base 124 by inserting the mating projections 120 into the sensor base 124. Once assembled, the physiological characteristic sensor assembly 102 may be packaged, in suitable packaging, for receipt by the consumer or user. Once received by the consumer or user, the sensor inserter 500 and the physiological characteristic sensor assembly 102 may be removed from the packaging.

Figure 24:
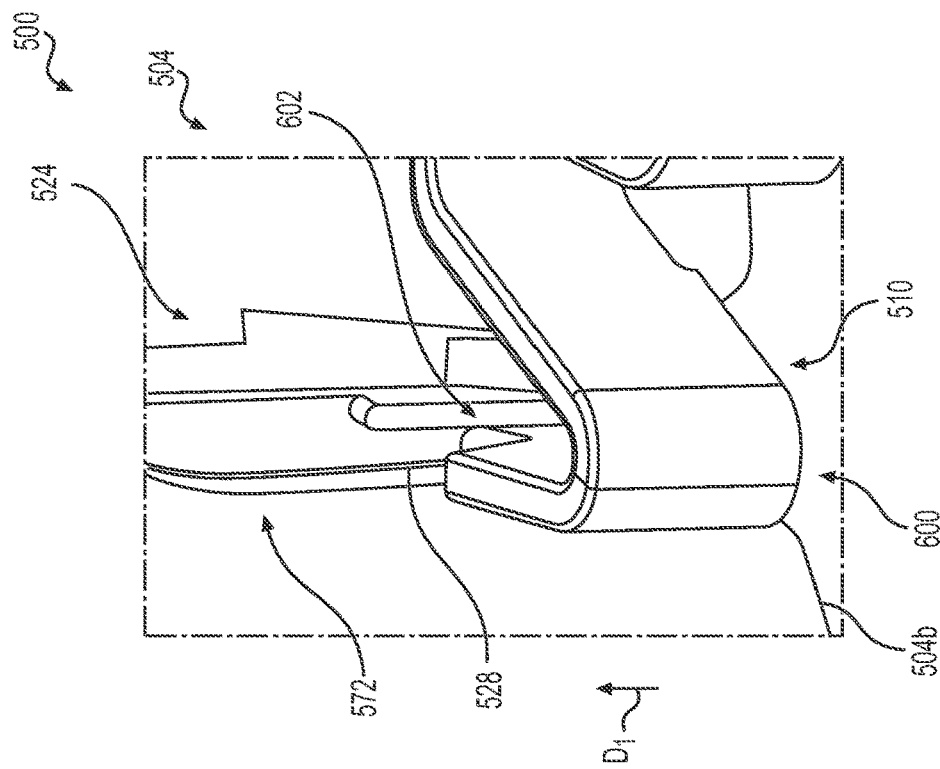
FIG. 24 is a detail view of the sensor inserter of FIG. 23, taken at 24 of FIG. 23.

An exemplary deployment methodology for the glucose sensor 122 will now be described with reference to FIGS. 23-30. FIGS. 23 and 24 are each a cross-sectional views of the sensor inserter 500, with the spring 202 and the pair of release tabs 508 removed for clarity. In one example, the sensor inserter 500 is placed over the physiological characteristic sensor assembly 102 and is pressed down to engage the sensor introducer 106 and to spring-load the insertion needle 118 as shown in FIG. 23A. In FIG. 23A, the packaging support 112 is removed for clarity. As the sensor introducer 106 is received within the sensor introducer receiving portion 270, with reference to FIGS. 23 and 24, the striker 506 is moved relative to the housing 504, in a direction towards the top surface 504a. As the striker 506 moves upward, in the direction D1, the spring 202 (not shown) is compressed. In addition, as the striker 506 moves in the direction D1, the tabs 602 move upward within the first tracks 522, as shown for one of the tabs 602 in FIG. 24. Generally, the sensor inserter 500 is pushed down over the physiological characteristic sensor assembly 102 until the sensor inserter 500 covers substantially all but the feet 112a of the packaging support 112 (FIG. 17), which causes the movement of the striker 506 from the first, shipping state to the second, cocked state such that the sensor inserter 500 has moved from the first, shipping state to the second, cocked state.

With reference to FIGS. 25 and 26, FIGS. 25 and 26 are each a cross-sectional views of the sensor inserter 500, with the spring 202 and the pair of release tabs 508 removed for clarity. As shown, as the sensor introducer 106 is received further within the sensor introducer receiving portion 270, the striker 506 continues to move relative to the housing 504, in the direction D1 towards the top surface 504a. As the striker 506 moves upward, in the direction D1, the spring 202 (not shown) is further compressed. In addition, as the striker 506 moves in the direction D1, the tabs 602 move upward within the first tracks 522 to the exits 530.

Figure 28:
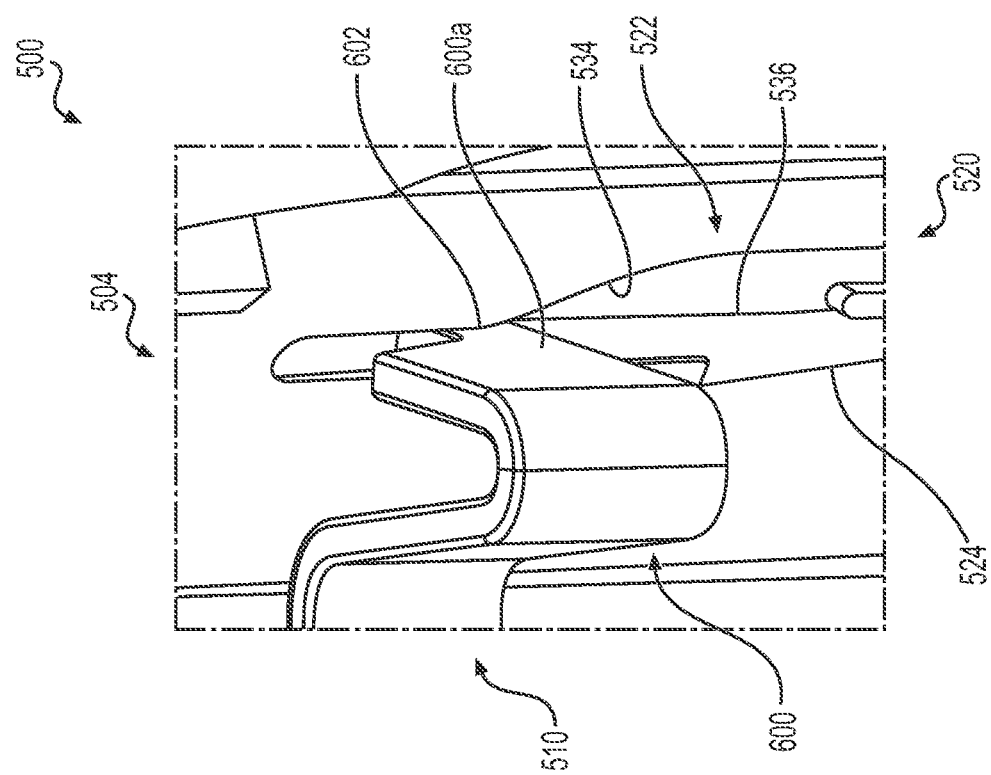
FIG. 28 is a detail view of the sensor inserter of FIG. 27, taken at 28 of FIG. 27.
Figure 27:
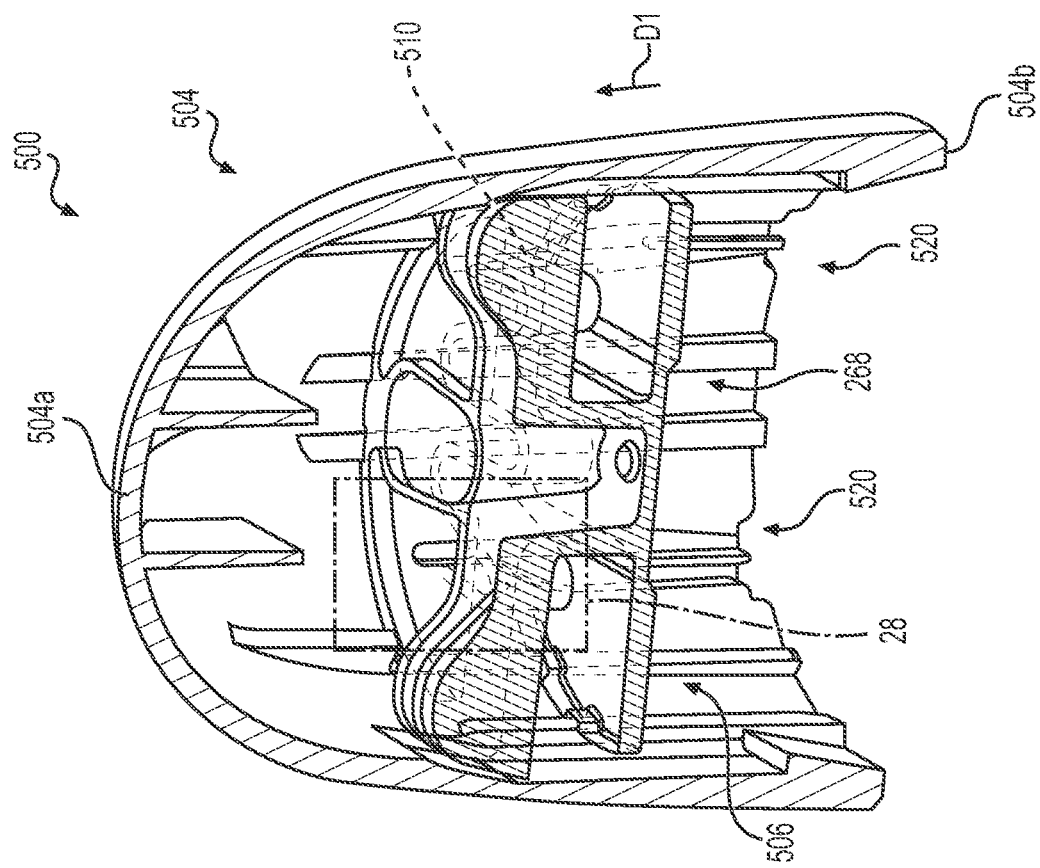
FIG. 27 is a cross-sectional view of the sensor inserter of FIG. 17, taken at line 21-21 of FIG. 17, which illustrates the sensor inserter in the second, cocked state.
Figure 28A:
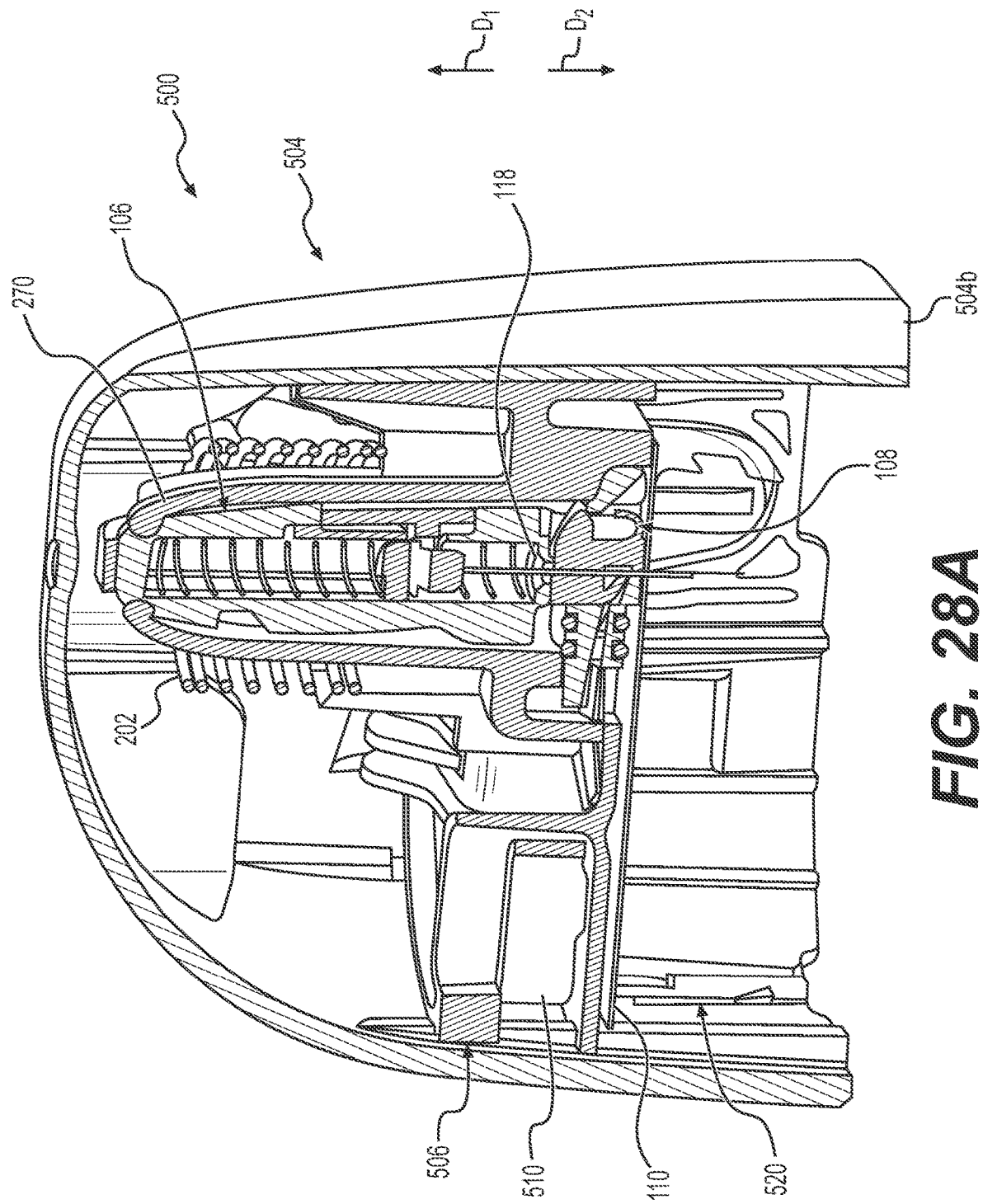
FIG. 28A is a cross-sectional view of the sensor inserter of FIG. 17, taken from the perspective of line 23B-23B of FIG. 23A, which illustrates the sensor inserter in the second, cocked state.

With reference to FIGS. 27, 28 and 28A, FIGS. 27 and 28 are each a cross-sectional views of the sensor inserter 500, with the spring 202 and the pair of release tabs 508 removed for clarity. FIG. 28A is a cross-sectional view taken from the perspective of line 23B-23B of FIG. 23A, which includes the sensor introducer 106, the physiological characteristic sensor 108 and the adhesive patch 110. In FIGS. 27, 28 and 28A, the sensor inserter 500 is in the second, cocked state. As shown, as the sensor inserter 500 is pushed over the sensor introducer 106, the sensor introducer 106 contacts the sensor introducer receiving portion 270, and the continued advancement of the sensor inserter 104 in a direction D2 over the physiological characteristic assembly 102 causes the striker 506 to move relative to the housing 504, in the direction D1 towards the top surface 504a into the second, cocked state. As discussed, generally, the sensor inserter 500 is advanced over the sensor introducer 106 until all but the feet 112a of the packaging support 112 (FIG. 1) extend beyond the bottom surface 504b of the housing 504. As the striker 506 moves in the direction D1, the spring 202 (FIG. 28A) is further compressed. In addition, as the striker 506 moves in the direction D1 to the second, cocked state, the second curved surface 534 (FIG. 28) of the first tracks 522 guide the tabs 602 from the first tracks 522 into the second tracks 524, as shown for one of the tabs 602 in FIG. 28. The first steps 536 (FIG. 28) inhibit the tabs 602 from re-entering the first tracks 522. In the second, cocked state, the tabs 602 are engaged with the second tracks 524 in the distances 546 of the second tracks 524 that extend beyond the first tracks 522 (FIG. 28).

With the sensor inserter 500 in the second, cocked state, the sensor inserter 500 may be removed from the packaging support 112 (not shown). The packaging support 112 (not shown) is separated from the other components of the physiological characteristic sensor assembly 102 by lifting the sensor inserter 500 away from the packaging support 112 while holding onto the feet 112a of the packaging support 112 (FIG. 17). Removal of the packaging support 112 exposes the adhesive patch 110 and the remainder of the physiological characteristic sensor assembly 102 is retained within the interior of the sensor inserter 500, ready for deployment on the skin of the user. After removing the packaging support 112 from the assembly, the user moves the sensor inserter 500 to the desired deployment location, holds the sensor inserter 500 against the skin, and actuates biasing tabs 212 of the housing 504 (see FIG. 20). Upon actuating of the biasing tabs 212, with reference to FIGS. 14 and 15, the striker 506 moves from the second, cocked state to the third, disposal state.

Figure 30:
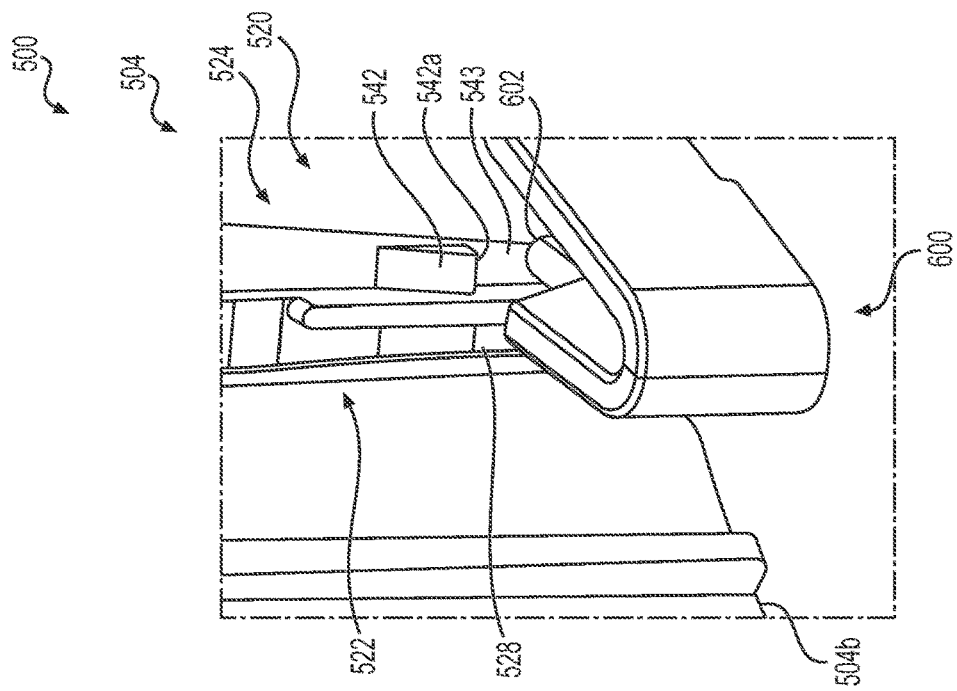
FIG. 30 is a detail view of the sensor inserter of FIG. 29, taken at 30 of FIG. 29.
Figure 29:
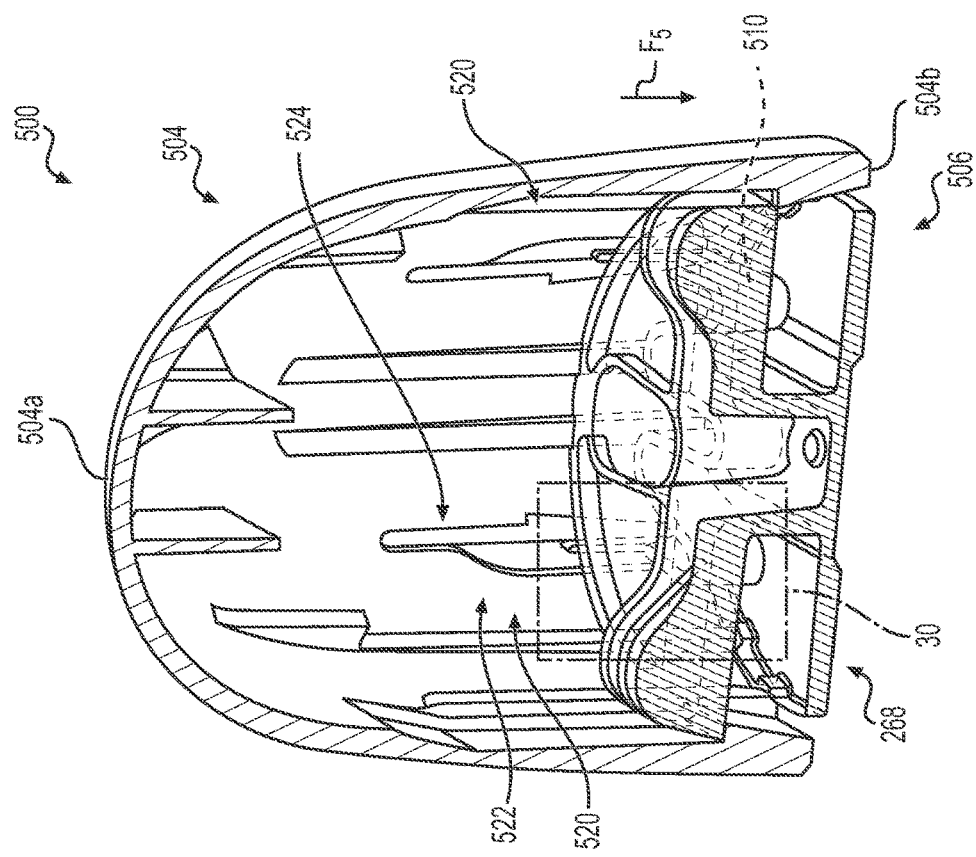
FIG. 29 is a cross-sectional view of the sensor inserter of FIG. 17, taken from the perspective of line 21-21 of FIG. 17, which illustrates the sensor inserter in a third, disposal state.

FIGS. 29 and 30 are each a cross-sectional views of the sensor inserter 500, with the spring 202 and the pair of release tabs 508 removed for clarity. In FIGS. 29 and 30, the sensor inserter 500 is in the third, disposal state. In the third, disposal state, the glucose sensor 122 (FIG. 1) is introduced to the anatomy and the adhesive patch 110 (FIG. 1) is coupled to the body of the user. In addition, in the third, disposal state, the sensor inserter 500 is inhibited from being reused to couple a replacement glucose sensor 122, for example, to the anatomy. As shown in FIGS. 29 and 30, actuation of the biasing tabs 212 compresses the biasing portion 312 of the release tabs 508 (FIG. 20), which moves the release tabs 508 from the stops 244. This enables the spring 202 to apply the spring force Fs to move the striker 506 from proximate the top surface 504a of the housing 504 to proximate the bottom surface 504b of the housing 504 to couple the glucose sensor 122 to the anatomy. As the striker 506 moves from the second, cocked state to the third, disposal state, the tabs 602 move along the second tracks 524 and over the ramps 542 into the second exits 543. The second steps 542a inhibit the tabs 602 from moving back up the second tracks 524. In the third, disposal state, the lock beam 510 is biased or compressed. The movement of the striker 506 from the second, cocked state to the third, disposal state also moves the adhesive patch 110 into contact with the user's skin, and activates the insertion needle 118 to insert the glucose sensor 122 into the skin. Thereafter, the sensor inserter 500 is removed and separated from the sensor introducer 106 and the glucose sensor 122, which remains affixed to the skin by way of the adhesive patch 110. The sensor introducer 106 may then be removed from the glucose sensor 122.

Figure 32:
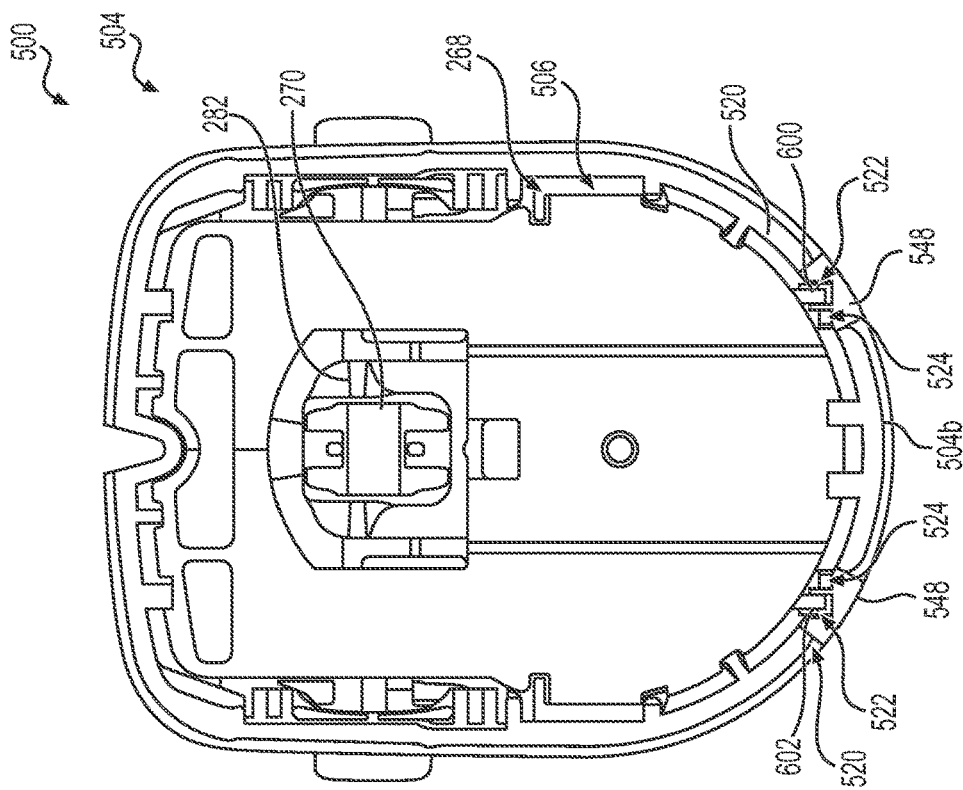
FIG. 32 is an end view of the sensor inserter of FIG. 17, which illustrates the sensor inserter reset from the third, disposal state to the first, shipping state.

In certain instances, the sensor inserter 500 may be moved from the first, shipping state to the second, cocked state and from the second, cocked state to the third, disposal state during manufacturing to ensure proper functioning of the sensor inserter 500. In these instances, with reference to FIGS. 31 and 32, a special tool is inserted into the passages 548 to push the tabs 602 out of the second exit 543. As the lock beam 510 is biased when the tabs 602 are in the second exit 543, the application of the force from the special tool causes the lock beam 510 to return to the relaxed or unbiased position, which is the position the lock beam 510 is in when the sensor inserter 500 is in the first, shipping state. Thus, the passages 548 enable the sensor inserter 500 to be moved from the third, disposal state to the first, shipping state during manufacturing by moving the tabs 602 from the second track 524 to the first track 522.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A sensor inserter for a physiological characteristic sensor, the sensor inserter comprising:
    a housing that defines a track system that extends from a bottom of the housing toward a top of the housing, the track system including a first track and a second track; and
    a striker assembly movable relative to the housing between a first state, a second, cocked state and a third, disposal state, the striker assembly movable from the second, cocked state to the third, disposal state to couple the physiological characteristic sensor to an anatomy, the striker assembly including a lock beam that engages with the track system as the striker assembly moves between the first state, the second, cocked state and the third, disposal state, and wherein:
        the lock beam engages the first track in the first state and moves from the first track to the second track as the striker assembly moves from the first state to the second, cocked state, and
        in the third, disposal state the lock beam inhibits movement of the striker assembly from the third, disposal state to the first state.

2. The sensor inserter of claim 1, wherein the striker assembly includes a striker, the lock beam is defined on the striker and the lock beam includes a body coupled to the striker and a tab cantilevered from the striker by the body.

3. The sensor inserter of claim 1, wherein the striker assembly includes a striker, the lock beam is coupled to a channel defined at an end of the striker and the lock beam includes a body having a plurality of undulations and a tab defined at one end of the body.

4. The sensor inserter of claim 1, wherein the lock beam directly contacts the track system.

5. The sensor inserter of claim 1, wherein the first track has an exit in communication with an entrance of the second track, and the lock beam moves from the exit of the first track to the entrance of the second track as the striker assembly moves from the first state to the second, cocked state.

6. The sensor inserter of claim 5, wherein a step is defined between the exit of the first track and the entrance of the second track to inhibit a movement of the lock beam from the entrance of the second track to the exit of the first track.

7. The sensor inserter of claim 5, wherein the second track defines a second step between the entrance of the second track and an exit of the second track, and the second step cooperates with the lock beam to inhibit the movement of the striker assembly from the third, disposal state to the first state.

8. The sensor inserter of claim 7, wherein the second step is defined by a ramp defined within the second track proximate the exit of the second track.

9. The sensor inserter of claim 1, wherein the second track is defined to extend a distance beyond the first track toward the top of the housing, and in the second, cocked state, the lock beam is positioned within the distance the second track extends beyond the first track.

10. The sensor inserter of claim 1, wherein in the lock beam engages with the second track in the second, cocked state and the third, disposal state.

11. The sensor inserter of claim 1, wherein the lock beam includes a tab that engages with the track system as the striker assembly moves relative to the housing.

12. The sensor inserter of claim 1, wherein the housing includes at least one reset passage to move the lock beam to reset the striker assembly from the third, disposal state to the first state.

13. The sensor inserter of claim 1, wherein the physiological characteristic sensor is a glucose sensor and the striker assembly is movable relative to the housing by a sensor introducer associated with the glucose sensor.

14. A sensor inserter for a physiological characteristic sensor, the sensor inserter comprising:
a housing that defines a track system that extends from a bottom of the housing toward a top of the housing, the track system including a first track and a second track; and
a striker assembly movable relative to the housing between a first state, a second, cocked state and a third, disposal state, the striker assembly movable from the second, cocked state to the third, disposal state to couple the physiological characteristic sensor to an anatomy, the striker assembly including a striker that defines a lock beam that engages with the first track in the first state and moves from the first track to the second track as the striker assembly moves from the first state to the second, cocked state, the lock beam remaining on the second track in the third, disposal state, the lock beam extending outwardly from a surface of the striker and including a tab that engages with the first track and the second track, and in the third, disposal state the lock beam inhibits movement of the striker assembly from the third, disposal state to the first state.

15. The sensor inserter of claim 1, wherein the lock beam comprises a body and a tab extending away from the body, and the tab is configured to slide along and within the first track and the second track.

16. The sensor inserter of claim 14, wherein a step is defined between an exit of the first track and an entrance of the second track to inhibit a movement of the lock beam from the entrance of the second track to the exit of the first track.

17. The sensor inserter of claim 14, wherein the second track includes an exit and a ramp defined within the second track proximate the exit of the first track, the ramp defines a second step between the entrance of the second track and the exit of the first track, and the second step cooperates with the lock beam to inhibit the movement of the striker assembly from the third, disposal state to the first state.

18. A sensor inserter for a physiological characteristic sensor, the sensor inserter comprising:
a housing that defines a track system that extends from a bottom of the housing toward a top of the housing, the track system including a first track and a second track; and
a striker assembly movable relative to the housing between a first state, a second, cocked state and a third, disposal state, the striker assembly movable from the second, cocked state to the third, disposal state to couple the physiological characteristic sensor to an anatomy, the striker assembly including a striker and a lock beam that engages with the first track in the first state and moves from the first track to the second track as the striker assembly moves from the first state to the second, cocked state, the lock beam remaining on the second track in the third, disposal state, the lock beam coupled to a channel defined at an end of the striker and including plurality of undulations and a tab that engages with the track system, and in the third, disposal state the lock beam inhibits movement of the striker assembly from the third, disposal state to the first state.

19. The sensor inserter of claim 18, wherein the lock beam engages with the first track in the first state, engages with the second track in the second, cocked state and the third, disposal state, and a step is defined between an exit of the first track and an entrance of the second track to inhibit a movement of the lock beam from the entrance of the second track to the exit of the first track.

20. The sensor inserter of claim 19, wherein the second track includes an exit and a ramp defined within the second track proximate the exit of the second track, the ramp defines a second step between the entrance of the second track and the exit of the second track, and the second step cooperates with the lock beam to inhibit the movement of the striker assembly from the third, disposal state to the first state.

* * * * *